(12) United States Patent
Ouerfelli et al.

(10) Patent No.: US 9,926,291 B2
(45) Date of Patent: Mar. 27, 2018

(54) SYNTHESIS OF THIOHYDANTOINS

(71) Applicant: Sloan-Kettering Institute for Cancer Research, New York, NY (US)

(72) Inventors: Ouathek Ouerfelli, Fort Lee, NJ (US); Anna Dilhas, Basel (CH); Guangbin Yang, Forest Hills, NY (US); Hong Zhao, Rego Park, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 15/370,093

(22) Filed: Dec. 6, 2016

(65) Prior Publication Data

US 2017/0081308 A1 Mar. 23, 2017

Related U.S. Application Data

(63) Continuation of application No. 14/666,933, filed on Mar. 24, 2015, now Pat. No. 9,512,103, which is a continuation of application No. 13/848,477, filed on Mar. 21, 2013, now Pat. No. 8,987,452, which is a continuation of application No. 12/450,423, filed as application No. PCT/US2008/058429 on Mar. 27, 2008, now Pat. No. 8,461,343.

(60) Provisional application No. 60/909,195, filed on Mar. 30, 2007, provisional application No. 60/908,280, filed on Mar. 27, 2007.

(51) Int. Cl.
| | | |
|---|---|---|
| *C07C 255/46* | (2006.01) |
| *C07D 401/04* | (2006.01) |
| *C07C 209/36* | (2006.01) |
| *C07C 213/08* | (2006.01) |
| *C07C 253/00* | (2006.01) |
| *C07C 253/30* | (2006.01) |
| *C07D 213/61* | (2006.01) |
| *C07D 213/64* | (2006.01) |
| *C07D 213/72* | (2006.01) |
| *C07D 213/74* | (2006.01) |
| *C07D 213/84* | (2006.01) |
| *C07C 231/12* | (2006.01) |
| *C07C 227/18* | (2006.01) |
| *C07D 213/643* | (2006.01) |
| *C07D 213/76* | (2006.01) |

(52) U.S. Cl.
CPC ......... *C07D 401/04* (2013.01); *C07C 209/36* (2013.01); *C07C 213/08* (2013.01); *C07C 227/18* (2013.01); *C07C 231/12* (2013.01); *C07C 253/00* (2013.01); *C07C 253/30* (2013.01); *C07D 213/61* (2013.01); *C07D 213/64* (2013.01); *C07D 213/643* (2013.01); *C07D 213/72* (2013.01); *C07D 213/74* (2013.01); *C07D 213/76* (2013.01); *C07D 213/84* (2013.01); *C07C 2601/04* (2017.05)

(58) Field of Classification Search
CPC .................................................... C07C 255/46
USPC ......................................................... 558/394
See application file for complete search history.

(56) References Cited

U.S. PATENT DOCUMENTS

| | | | |
|---|---|---|---|
| 5,968,875 A | 10/1999 | Bis et al. |
| 8,445,507 B2 | 5/2013 | Jung et al. |
| 8,461,343 B2 | 6/2013 | Ouerfelli et al. |
| 8,987,452 B2 | 3/2015 | Ouerfelli et al. |
| 9,512,103 B2 | 12/2016 | Ouerfelli et al. |
| 2004/0077605 A1 | 4/2004 | Salvati et al. |
| 2007/0004753 A1 | 1/2007 | Sawyers et al. |
| 2011/0003839 A1 | 1/2011 | Jung et al. |
| 2013/0072511 A1 | 3/2013 | Jung et al. |
| 2015/0133481 A1 | 5/2015 | Dilhas et al. |

FOREIGN PATENT DOCUMENTS

| | | |
|---|---|---|
| CN | 101032483 | 9/2007 |
| EP | 1 632 477 A | 3/2006 |
| WO | WO 2006/124118 A1 | 11/2006 |
| WO | WO 2007/126765 A1 | 11/2007 |
| WO | WO 2007/127010 A1 | 11/2007 |
| WO | WO 2013/184681 A1 | 12/2013 |

OTHER PUBLICATIONS

International Search Report and Written Opinion, dated Jul. 27, 2009 in connection with Application No. PCT/US2008/058429.
International Preliminary Report on Patentability, dated Oct. 8, 2009 in connection with Application No. PCT/US2008/058429.
International Search Report and Written Opinion, dated Sep. 27, 2013 in connection with Application No. PCT/US2013/044116.
International Preliminary Report on Patentability, dated Dec. 18, 2014 in connection with Application No. PCT/US2013/044116.
Chen et al., Molecular determinants of resistance to antiandrogen therapy. Nat Med. Jan. 2004;10(1):33-9. Epub Dec. 21, 2003.
Chobanian et al., A facile microwave-assisted palladium-catalyzed cyanation of aryl chlorides. Tetrahed Lett. May 8, 2006;47(19):3303-5.
Kagabu, Methyl, trifluoromethyl, and methoxycarbonyl—introduction to the fifth position on the pyridine ring of chloronicotinyl insecticide imidacloprid. Synth Comm. 2006;36(9):1235-45.
Jung et al., Structure-activity relationship for thiohydantoin androgen receptor antagonists for castration-resistant prostate cancer (CRPC). J Med Chem. Apr. 8, 2010;53(7):2779-96. doi: 10.1021/jm901488g. Epub Sep. 27, 2011. 59 pages.

(Continued)

*Primary Examiner* — Patricia L Morris
(74) *Attorney, Agent, or Firm* — Wolf, Greenfield & Sacks, P.C.

(57) ABSTRACT

A novel synthesis of the anti-androgen, A52, which has been found to be useful in the treatment of prostate cancer, is provided. A52 as well as structurally related analogs may be prepared via the inventive route. This new synthetic scheme may be used to prepare kilogram scale quantities of pure A52.

8 Claims, 1 Drawing Sheet

(56) References Cited

OTHER PUBLICATIONS

Kawai et al., Site-specific fluorescent labeling of RNA molecules by specific transcription using unnatural base pairs. J Am Chem Soc. Dec. 14, 2005;127(49):17286-95.

Kuethe et al., Synthesis of disubstituted imidazo[4,5-b]pyridin-2-ones. J Org Chem. Oct. 29, 2004;69(22):7752-4.

Takemoto et al., Novel potassium channel openers: synthesis and pharmacological evaluation of new N-(substituted-3-pyridyl)-N'-alkylthioureas and related compounds. J Med Chem. Jan. 7, 1994;37(1):18-25.

Yoshino et al., Design and synthesis of an androgen receptor pure antagonist (CH5137291) for the treatment of castration-resistant prostate cancer. Bioorg Med Chem. Dec. 1, 2010;18(23):8150-7. doi: 10.1016/j.bmc.2010.10.023. Epub Oct. 15, 2010.

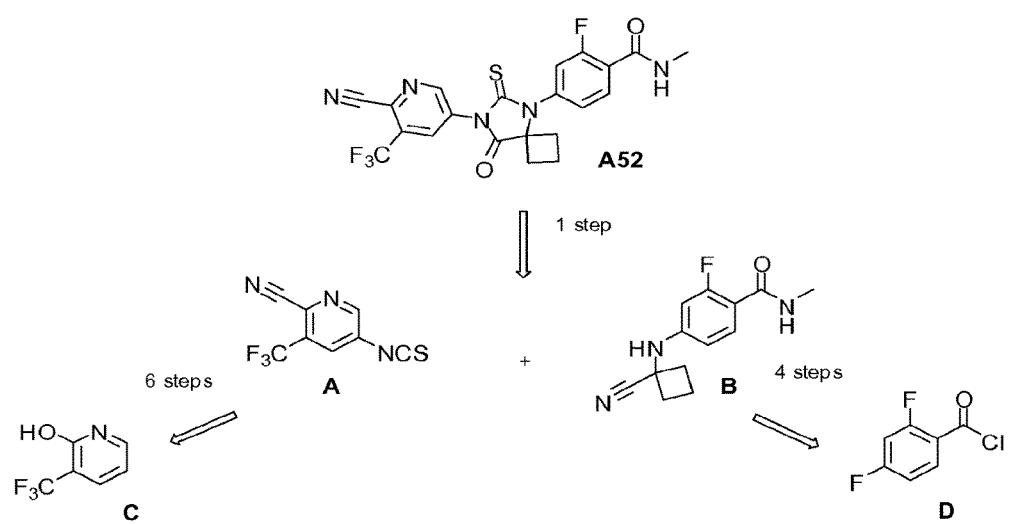

SYNTHESIS OF THIOHYDANTOINS

RELATED APPLICATIONS

The present application is a continuation of and claims priority under 35 U.S.C. § 120 to U.S. patent application Ser. No. 14/666,933, filed Mar. 24, 2015, which claims priority under 35 U.S.C. § 120 to and is a continuation of U.S. patent application U.S. Ser. No. 13/848,477, filed Mar. 21, 2013, which claims priority under 35 U.S.C. § 120 to and is a continuation of U.S. patent application U.S. Ser. No. 12/450,423, filed Apr. 5, 2010, which claims priority to and is a national stage filing under 35 U.S.C. § 371 of international PCT application, PCT/US2008/058429, filed Mar. 27, 2008, which claims priority under 35 U.S.C. § 119(e) to U.S. provisional patent applications, U.S. Ser. No. 60/908,280, filed Mar. 27, 2007, and U.S. Ser. No. 60/909,195, filed Mar. 30, 2007, each of which is incorporated herein by reference.

GOVERNMENT SUPPORT

This invention was made with government support under grant number CA008748 awarded by the National Institutes of Health. The government has certain rights in the invention.

BACKGROUND OF THE INVENTION

Prostate cancer is one of the most common forms of cancer found in Western men and the second leading cause of cancer death in Western men. When prostate cancer is confined locally, the disease can usually be treated by surgery and/or radiation. Advanced disease is frequently treated with anti-androgen therapy, also known as androgen deprivation therapy. Administration of anti-androgens blocks androgen receptor (AR) function by competing for androgen binding; and therefore, anti-androgen therapy reduces AR activity. Frequently, such therapy fails after a time, and the cancer becomes hormone refractory, that is, the prostate cancer no longer responds to hormone therapy and the cancer does not require androgens to progress.

Overexpression of AR has been identified as a cause of hormone refractory prostate cancer (*Nat. Med.*, 10:33-39, 2004; incorporated herein by reference). Overexpression of AR is sufficient to cause progression from hormone sensitive to hormone refractory prostate cancer, suggesting that better AR antagonists than the current drugs may be able to slow the progression of prostate cancer. It has been demonstrated that overexpression of AR converts anti-androgens from antagonists to agonists in hormone refractory prostate cancer. This work explains why anti-androgen therapy fails to prevent the progression of prostate cancer.

The identification of compounds that have a high potency to anatgonize AR activity would overcome the hormone refractory prostate cancer and slowdown the progression of hormone sensitive prostate cancer. Such compounds have been identified by Sayers et al. (WO 2007/126765, published Nov. 8, 2007; which is incorporated herein by reference). One compound is known as A52, a biarylthiohydantoin, and has the chemical structure:

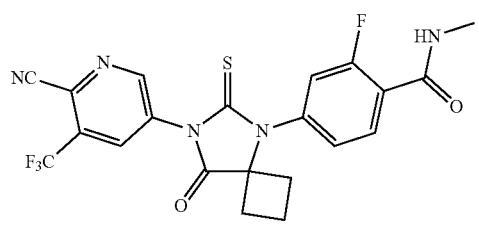

Another compound A51 has the chemical structure:

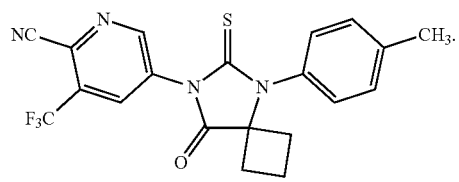 [SMILES: Cc1ccc(N2C(=S)N(c3cnc(C#N)c(C(F)(F)F)c3)C(=O)C23CCC3)cc1]

Both of these compounds share the same western and central portions. Given the need for larger quantities of pure A51 and A52 for pre-clinical and clinical studies, there remains a need for a more efficient synthesis of the compound from commercially available starting materials.

SUMMARY OF THE INVENTION

The present invention provides synthetic methodology and useful intermediates for preparing thiohydantoins. The inventive methodology is particularly useful in the synthesis of biarylthiohydantoins. In certain embodiments, the compounds are anti-androgen compounds useful in the treatment of cancer, such as A51 and A52. The inventive synthesis provides routes to useful intermediates in the synthesis of these compounds as well as the final product (e.g., A51, A52). In particular, the invention provides a more efficient to A52 than was previously known. The synthesis is based on the retrosynthetic analysis of the exemplary compound A52 as shown in FIG. 1. In particular, two intermediates, 3-(trifluoromethyl)-5-isothiocyanatopyridine-2-carbonitrile and 4-(1-cyano-1-cyclobutylamino)-2-fluoro-N-methylbenzamide, are prepared and coupled together to form the compound A52. As would be appreciated by one of skill in the art, the synthetic methods and intermediates may be modified to prepare analogs of A52 such as other biarylthiohydantoins.

In one aspect, the invention provides a novel synthesis of 3-(trifluoromethyl)-5-isothiocyanatopyridine-2-carbonitrile. In certain embodiments, the method of synthesizing 3-(trifluoromethyl)-5-isothiocyanatopyridine-2-carbonitrile comprises:

(a) chlorinating a 5-nitropyridine of formula:

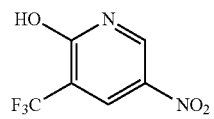

under suitable conditions (e.g., $POCl_3/PCl_5$) to provide a compound of formula:

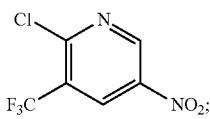

(b) cyanating the resulting 2-chloropyridine of step (a) under suitable conditions (e.g., a palladium catalyst and source of cyanide) to provide a compound of formula:

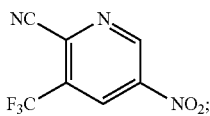

(c) reducing the nitro group of the compound from step (b) under suitable conditions (e.g., iron powder) to provide an amine of formula:

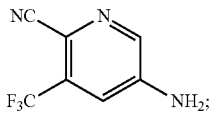

and (d) converting the amino of step (c) under suitable conditions (e.g., thiophosgene) to the corresponding isothiocyanate of formula:

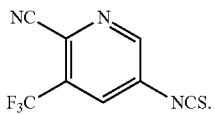

In certain embodiments, the method of synthesizing 3-(trifluoromethyl)-5-isothiocyanatopyridine-2-carbonitrile comprises:

(a) halogenating a compound of formula:

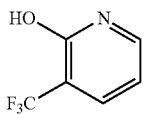

under suitable conditions (e.g., N-iodosuccinimide or N-bromosuccinimide) to provide a compound of formula:

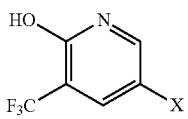

wherein X is bromine or iodine;

(b) chlorinating the resulting halogenated compound of step (a) under suitable conditions (e.g., POCl$_3$) to provide a compound of formula:

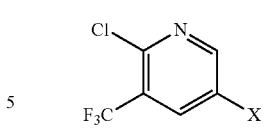

wherein X is bromine or iodine;

(c) aminating the resulting compound of step (b) under suitable conditions (e.g., palladium catalyst and amine) to provide a compound of formula:

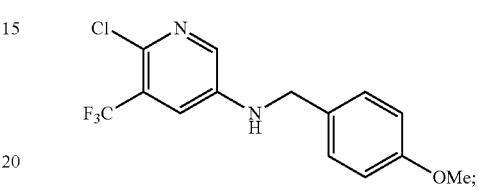

(d) cyanating the resulting 2-chloropyridine of step (c) under suitable conditions (e.g., palladium catalyst and source of CN) to provide a compound of formula:

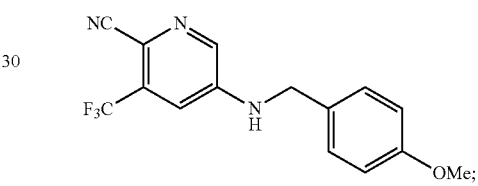

(e) deprotecting the resulting amine of step (d) under suitable conditions (e.g., TFA) to provide a compound of formula:

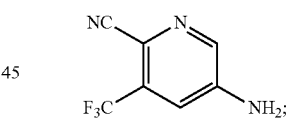

and (f) converting the 5-aminopyridine of step (e) under suitable conditions (e.g., thiophosgene) to the corresponding isothiocyanate of formula:

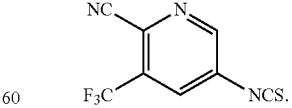

In another aspect, the invention provides a synthesis of 4-(1-cyano-1-cyclobutylamino)-2-fluoro-N-methylbenzamide. In certain embodiments, the method of synthesizing 4-(1-cyano-1-cyclobutylamino)-2-fluoro-N-methylbenzamide comprises reacting a compound of formula:

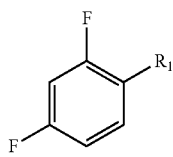

wherein $R_1$ is a substituted or unsubstituted acyl moiety or —CN, with

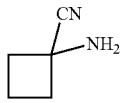

under suitable conditions to provide a compound of formula:

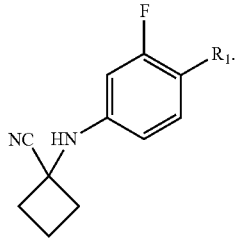

In certain embodiments, the method of synthesizing 4-(1-cyano-1-cyclobutylamino)-2-fluoro-N-methylbenzamide comprises reacting a compound of formula:

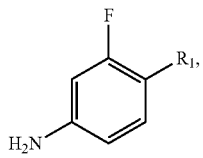

wherein $R_1$ is a substituted or unsubstituted acyl moiety or —CN, with

and a source of cyanide (CN) under suitable conditions to provide a compound of formula:

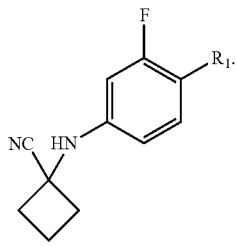

In another aspect, the present invention provides a method of synthesizing A52 by coupling 3-(trifluoromethyl)-5-isothiocyanatopyridine-2-carbonitrile with 4-(1-cyano-1-cyclobutylamino)-2-fluoro-N-methylbenzamide. In certain embodiments, the synthetic method comprises coupling a substituted pyridine of formula:

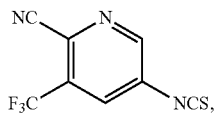

with a compound of formula:

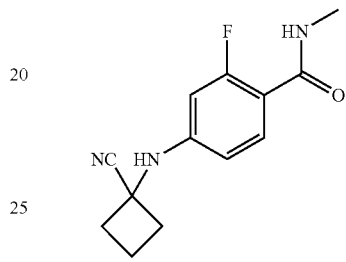

under suitable conditions to form a product of formula:

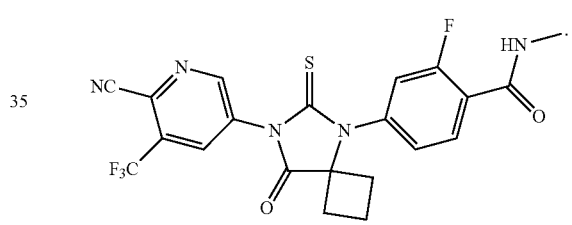

The final product may be purified by recrystallization from ethanol to provide pure material suitable for pre-clinical or clinical studies. The synthetic methodology described herein may be scaled up to produce 1 kg or more of pure A52.

In another aspect, the present invention provides novel intermediates useful in the synthesis of A52. In certain embodiments, the intermediate is of formula:

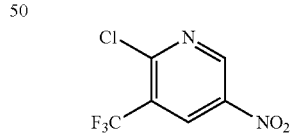

In certain embodiments, the intermediate is of the formula:

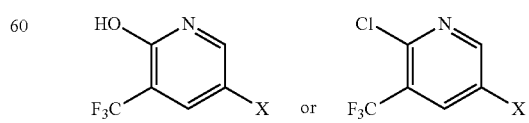

wherein X is halogen. In certain embodiments, the intermediate is of the formula:

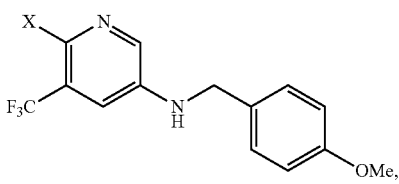

wherein X is halogen or —CN.

The novel synthesis of A52 and analogues thereof provides pure compound in a more efficient route than previous syntheses of this compound. The inventive syntheses are scalable allowing for the production of kilogram quantities of the desired final product.

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex mixtures of isomers.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer or diastereomer. Alternatively, where the molecule contains a basic functional group, such as an amino group, or an acidic functional group, such as a carboxylic acid group, diastereomeric salts are formed with an appropriate optically-active acid or base, followed by resolution of the diastereomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4,4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed., Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine, and iodine.

"Independently selected": The term "independently selected" is used herein to indicate that the R groups can be identical or different.

"Labeled": As used herein, the term "labeled" means that a compound comprises at least one element, isotope, or chemical compound to enable the detection of the compound by any technique that would enable detection. Labels may be: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; or c) colored, luminescent, phosphorescent, or fluorescent dyes. It will be appreciated that the labels incorporated into the compound at any position that does not substantially interfere with the biological activity or characteristic of the compound that is being detected. In other embodiments such as in the identification of the biological target of a natural product or derivative thereof, the compound is labeled with a radioactive isotope, preferably an isotope which emits detectable particles, such as β particles. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

BRIEF DESCRIPTION OF THE DRAWING

FIG. 1 shows a retrosynthetic analysis of the thiohydantoin, A52.

DETAILED DESCRIPTION OF CERTAIN EMBODIMENTS OF THE INVENTION

A new synthesis of biarylthiohydantoins and intermediates thereto is provided herein. This new synthetic methodology has been developed specifically to provide a more efficient synthetic route to the anti-androgen, A52. However, as would be appreciated by an organic chemist, the methodology can also be applied to other compounds including the related compound A51. The synthesis of other thiohydantoins, particularly biarylthiohydantoins of the formula:

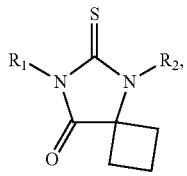

wherein each of R₁ and R₂ is independently a substituted or unsubstituted aryl moiety; or substituted or unsubstituted heteroaryl moiety, may also benefit from the synthetic methods and/or intermediates disclosed herein.

Synthesis of Western Portion

As shown in FIG. 1 which includes a retrosynthetic analysis of A52, the compound is essentially prepared by coupling the two halves of the molecule (compounds A and B) to form the final product. One of the first improvements in the synthesis of A52 stems from a shorter and more efficient synthesis of compound A, which is used for the western portion of the final product. As shown below, Compound A (3-(trifluoromethyl)-5-isothiocyanatopyridine-2-carbonitrile) is prepared from nitropyridone E by chlorination, palladium-catalyzed cyanation of the resulting chlorine, selective reduction of the nitro group, and finally conversion of the resulting amine to an isothiocyanate.

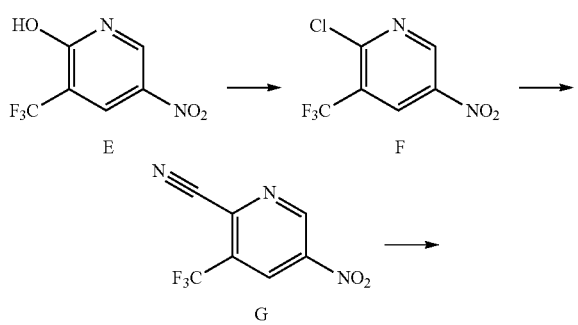

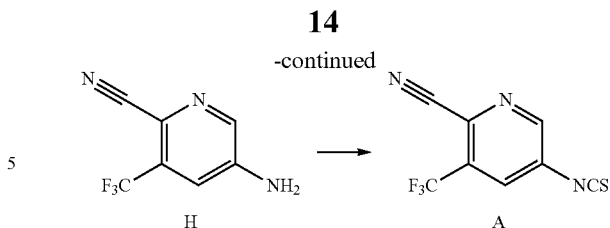

In certain embodiments, the invention provides novel methods of preparing compound A from nitropyridone E. In certain embodiments, the synthetic method includes:

(a) chlorinating a compound of formula:

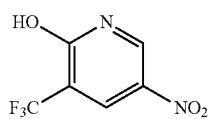

under suitable conditions (e.g., SOCl₂, POCl₃/PCl₅, POCl₃, PhPOCl₂) to provide a compound of formula:

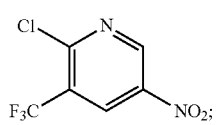

(b) cyanating the 2-chloropyridine resulting from step (a) under suitable conditions (e.g., palladium catalyst and Zn(CN)₂, tri-n-butyltincyanide, Cu(I)CN, potassium hexacyanoferrate (II)) to provide a compound of formula:

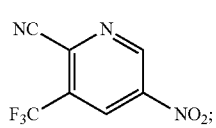

(c) selectively reducing the nitro group of the compound resulting from step (b) under suitable conditions (e.g., dissolved Fe(0)) to provide an amine of formula:

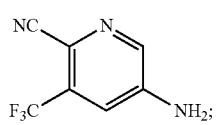

and (d) converting the compound resulting from step (c) under suitable conditions (e.g., thiophosgene in the presence base) to the corresponding isothiocyanate of formula:

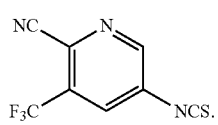

As would be appreciated by one of skill in the art, the aryl ring may include other substituents and the substitution pattern about the ring may differ from the compounds shown above. In certain embodiments, other aryl rings besides pyridinyl are used in the above synthetic methods. For example, a phenyl ring or pyrimidinyl ring may be used. Although six-membered aryl rings are shown in the schemes detailed herein, five-membered heteroaryl rings may also be used.

The individual steps in the synthesis of compound A may also be performed separately in order to prepare compound A or another substituted aromatic compound. As will be appreciated by one of skill in the art, each of the reaction described herein may optionally be followed by one or more purification steps (e.g., recrystallization, column chromatography, distillation, extraction, filtration). In certain embodiments, the invention provides a method comprising the step of chlorinating a 5-hydroxypyridine of formula:

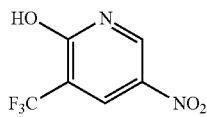

under suitable conditions to provide a compound of formula:

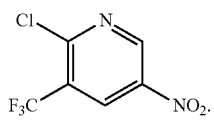

In certain particular embodiments, the chlorination step is performed using $POCl_3/PCl_5$. In certain particular embodiments, the chlorination step is performed using $POCl_3$. In certain embodiments, instead of a chlorination step, a bromination step is used in the synthesis of Compound A or the intermediate of formula:

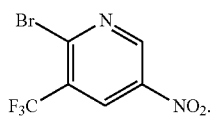

In certain embodiments, the method includes the step of cyanating a 2-chloropyridine of formula:

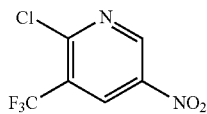

under suitable conditions to provide a compound of formula:

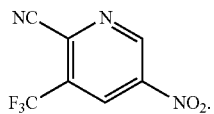

In certain particular embodiments, the cyanation step is a palladium-catalyzed cyanation. In certain embodiments, the palladium catalyst is $Pd_2(dba)_2$ with ligand. In certain embodiments, the palladium catalyst is $Pd(OAc)_2$ with ligand. In certain embodiments, the cyanation step is performed in the presence of $Pd_2(dba)_2$, the ligand 1,1'-bisdiphenylphosphinoferrocene (dppf), and $Zn(CN)_2$. In certain embodiments, the amount of catalyst used ranges from about 0.1 mol % to about 20 mol %. Other palladium catalysts (including ligand) or sources of cyanide (e.g., NaCN, KCN, Cu(CN), $K_4[Fe(CN)_6]$, tri-n-butyltincyanide) may also be used. In certain embodiments, the reaction is performed in DMF as the solvent. The reaction may be irradiated with microwaves in order to effect the transformation. In certain embodiments, the reaction mixture is heated to effect the transformation. In certain embodiments, the reaction is run at a temperature ranging from approximately 100° C. to approximately 150° C. In certain embodiments, the reaction is run at approximately 130° C. In certain embodiments, a bromopyridine of formula:

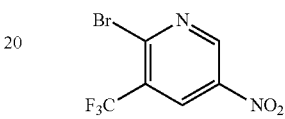

is used as the starting material in the inventive cyanation reaction.

In certain embodiments, the method of reducing the nitro group includes selectively reducing the nitro group of a 5-nitropyridine of formula:

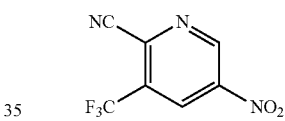

under suitable conditions to provide a compound of formula:

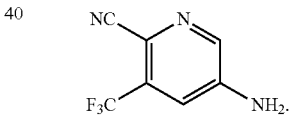

This reduction of the nitro group is done in the presence of a nitrile which is also susceptible to reduction. Preferably, the conditions of the reduction step are such that the nitro group is reduced without substantially reducing the nitrile group. In certain embodiments, less than about 10%, less than about 5%, less than about 2%, or less than about 1% of the nitrile groups are reduced. In certain embodiments, the reduction is done with dissolved iron. In certain embodiments, the reduction is performed using iron powder (or other form of iron) dissolved in acetic acid (or other acid such as HCl) and a solvent (e.g., ethyl acetate). In certain embodiments, at least 2 equivalents of iron are used. In certain embodiments, approximately 5 equivalents of iron are used. Other metals besides iron may also be used in this reduction step. In certain embodiments, the reaction is performed at room temperature. In certain embodiments, the reaction mixture is heated. In certain embodiments, the reaction is performed at approximately 60-75° C. In certain embodiments, the reaction is performed at approximately 65° C. In certain embodiments, the reduction of the nitro group is performed using a Raney nickel-catalyzed hydrogenation.

In certain embodiments, the invention provides a method of converting the amino group to an isothiocyanate. In certain embodiments, the method comprises converting the amino group of a 5-aminopyridine of formula:

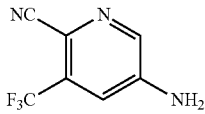

under suitable conditions to provide an isothiocyanate of formula:

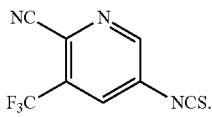

In certain embodiments, the conversion is performed using thiophosgene. In certain embodiments, the conversion is performed using thiophosgene in the presence of base. This reaction may be carried out in water as solvent at room temperature.

While the above route to Compound A is shorter than those previously reported (see WO 2007/126765, published Nov. 8, 2007), yet another route was developed to provide a better precursor to the amino group at position 5 of Compound A. This new route begins with 2-trifluoromethyl-2-pyridone (C), which is converted into 5-iodo-3-trifluoromethyl-2-pyridone or the 5-bromo analog. The halogen anchors the position for the amino group of Compound A. The halogen may be replaced by another suitable leaving group such as a triflate. As shown below, Compound A may be prepared by halogenation of 3 trifluoromethyl-2-pyridone (C), chlorination of the hydroxyl group, and two successive, selective palladium-catalyzed substitutions. The first palladium-catalyzed reaction places an amine (e.g., benzylamine, dibenzylamine, 4-methoxybenzylamine, N,N-bis(4-methoxybenzyl)amine) at position 5. The amine may be unprotected, monoprotected (e.g., benzylamine), or diprotected (e.g., dibenzylamine). In certain embodiments, the amine is introduced as a free amino group. In certain embodiments, the amine is introduced as a protected amine. The second introduces the cyano group. If present, the protecting group on the protected amine is removed, and the unprotected amino group is converted to a thiocyanate as described above. While this route requires more steps, this sequence can be performed on a larger scale than previously reported syntheses of Compound A.

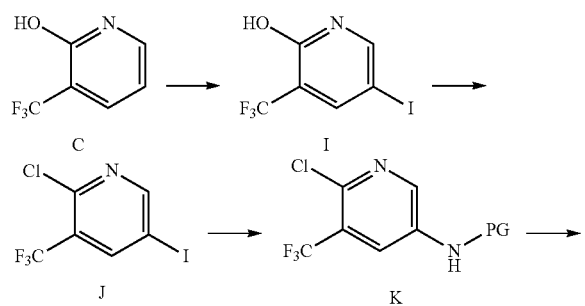

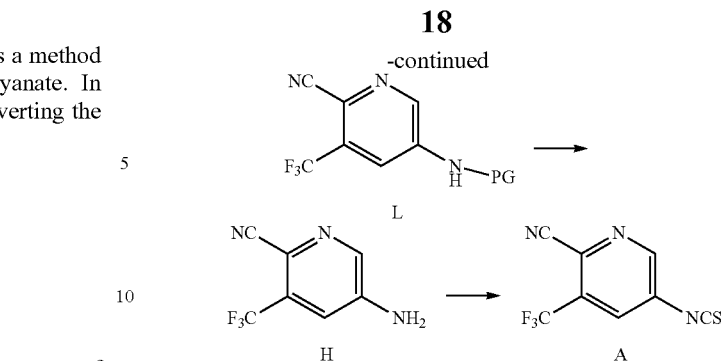

In certain embodiments, the invention provides novel methods of preparing compound A from 3-trifluoromethyl-2-pyridone C. In certain embodiments, the synthetic method includes the steps of:

(a) halogenating a compound of formula:

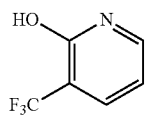

under suitable conditions (e.g., N-iodosuccinimide (NIS), N-bromosuccinimide (NBS)) to provide a compound of formula:

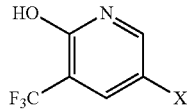

wherein X is bromine or iodine;

(b) chlorinating the resulting halogenated compound of step (a) under suitable conditions (e.g., POCl$_3$) to provide a compound of formula:

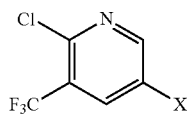

wherein X is bromine or iodine;

(c) aminating the resulting compound of step (b) under suitable conditions (e.g., palladium-catalyzed amination) to provide a compound of formula:

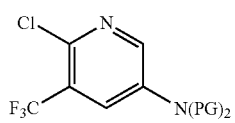

wherein each PG is independently hydrogen or a suitable amine protecting group (e.g., benzyl, methoxybenzyl, 4-methoxybenzyl);

(d) cyanating the resulting 2-chloropyridine of step (c) under suitable conditions (e.g., palladium-catalyzed cyanation) to provide a compound of formula:

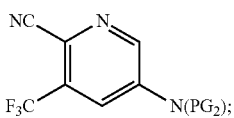

(e) deprotecting the amine of the compound of step (d) under suitable conditions to provide a compound of formula:

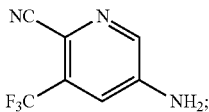

and (f) converting the 5-aminopyridine of step (e) under suitable conditions to the corresponding isothiocyanate of formula:

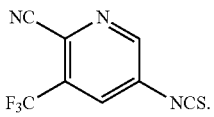

As would be appreciated by one of skill in the art, the aryl ring may include other substituents and the substitution pattern about the ring may differ from the compounds shown above. In certain embodiments, other aryl rings besides pyridinyl are used in the above synthetic methods. For example, a phenyl ring or pyrimidinyl ring may be used. Although six-membered aryl rings are shown in the schemes detailed herein, five-membered heteroaryl rings may also be used.

The individual steps in this alternative synthesis of compound A may also be performed separately in order to prepare compound A or another substituted aromatic compound. For example, in certain embodiments, the method includes halogenating a substituted pyridine of formula:

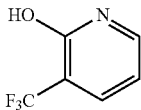

under suitable conditions to provide a compound of formula:

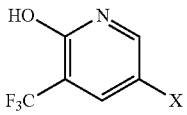

wherein X is bromine or iodine. Besides halogens such as bromine and iodine, other suitable leaving groups such as triflate, tosylate, and like may be used in a subsequent nucleophilic displacement substitution, or transition metal-catalyzed amination, alkyl amination, or carbamoylation. In the case wherein X is iodine, N-iodosuccinimide (NIS) may be used as the iodinating reagent. In the case wherein X is bromine, N-bromouccinimide (NIS) may be used as the brominating reagent. In certain embodiments, the halogenation reaction is performed in a mixture of acetonitrile and DMF at approximately 80° C. In certain embodiments, the solvent for the reaction is acetonitrile:DMF (1:1).

In certain embodiments, the step of converting the hydroxyl group of 5-halo-3-trifluoromethyl-2-pyridinol to a chlorine includes chlorinating a compound of formula:

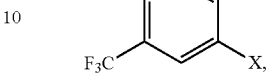

wherein X is bromine or iodine, under suitable condition to provide a compound of formula:

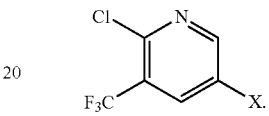

In certain embodiments, the chlorination reaction is performed using $POCl_3$. In certain embodiments, the chlorination reaction is performed using $POCl_3/PCl_5$. In certain embodiments, DMF is used as the solvent in the chlorination reaction. In certain embodiments, reaction mixture is irradiated with microwaves to effect the chlorination. In certain embodiments, the reaction mixture is heated to a temperature ranging from about 100° C. to about 150° C. In certain embodiments, the reaction is heated to approximately 110° C. In certain embodiments, the reaction is heated to approximately 120° C. In certain embodiments, the reaction is heated to approximately 130° C.

In certain embodiments, the iodine, bromine, or other suitable leaving group is replaced with an amine via a transition metal-catalyzed reaction (e.g., palladium-catalyzed reaction). In certain embodiments, the method includes aminating a compound of formula:

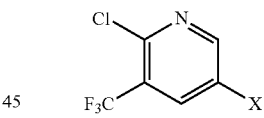

wherein X is bromine or iodine, under suitable conditions to provide a compound of formula:

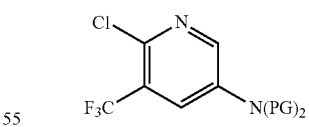

wherein each PG is independently hydrogen or a nitrogen protecting group. In certain embodiments, the method includes aminating a compound of formula:

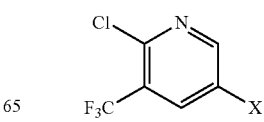

wherein X is bromine or iodine, under suitable conditions to provide a compound of formula:

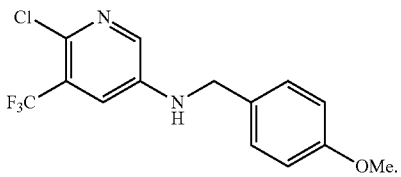

The amination reaction is preferably selective for position 5. In certain embodiments, the chlorine at position 2 is unaffected. Other nitrogen-protecting groups besides 4-methoxybenzyl may be used for introducing the amine. In certain embodiments, the protecting group is benzyl. In certain embodiments, the protecting group is methoxybenzyl. In certain embodiments, the amine is doubly protected. In certain embodiments, the amine is introduced as an unprotected amino group (—NH$_2$). In certain embodiments, the amine is introduced as an amide. In certain embodiments, the amine is introduced as a carbamate. Active amides, cabamates (e.g., tertiobutylcarbamate, benzylcarbamate), and amines that are deprotected by fluoride ion are also useful. In certain embodiments, the reaction is catalyzed by a palladium catalyst. In certain embodiments, the reaction is performed in the presence of Pd(OAc)$_2$, BINAP, Et$_3$N, and Cs$_2$CO$_3$. In certain embodiments, the reaction is performed in the presence of Pd$_2$(dba)$_3$, Xantphos, and sodium tert-butoxide. In certain embodiments, the amount of catalyst used ranges from about 0.1 mol % to about 5 mol %. In certain embodiments, the amine used is 4-methoxybenzylamine. In certain embodiments, the reaction is performed in refluxing toluene. In certain embodiments, the reaction mixture is irradiated with microwaves.

In certain embodiments, the invention provides method of cyanating. In certain embodiments, the method includes cyanating a compound of formula:

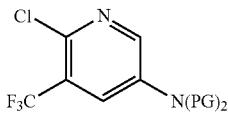

wherein each PG is independently hydrogen or a suitable nitrogen-protecting group, under suitable conditions to provide a compound of formula:

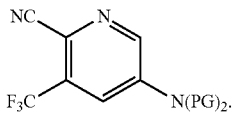

In certain embodiments, the cyanation step is palladium-catalyzed. In certain embodiments, the palladium catalyst is Pd$_2$(dba)$_2$ with ligand. In certain embodiments, the palladium catalyst is Pd(OAc)$_2$ with ligand. In certain embodiments, the cyanation step is performed in the presence of Zn(CN)$_2$, Pd$_2$(dba)$_3$, and the ligand 1,1'-bis(diphenylphosphino)ferrocene (dppf). In certain embodiments, the amount of catalyst used ranges from about 0.1 mol % to about 20 mol %. Other palladium catalysts (including ligand) or sources of cyanide (e.g., NaCN, KCN, Cu(CN), K$_4$[Fe(CN)$_6$], tri-n-butyltincyanide) may also be used. In certain embodiments, the reaction is performed in DMF as the solvent. The reaction may be irradiated with microwaves in order to effect the transformation. In certain embodiments, the reaction mixture is heated to effect the transformation. In certain embodiments, the reaction is run at a temperature ranging from approximately 100° C. to approximately 150° C. In certain embodiments, the reaction mixture is heated to approximately 110° C. In certain embodiments, the reaction mixture is heated to approximately 120° C. In certain embodiments, the reaction is run at approximately 130° C. In certain embodiments, the reaction mixture is irradiated with microwaves.

In certain embodiments, the invention provides a method of deprotecting the protected amine of formula:

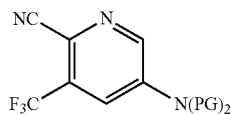

under suitable conditions to provide a compound of formula:

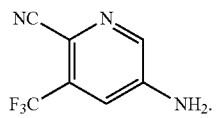 [SMILES: N#Cc1ncc([N+](=O)[O-])cc1C(F)(F)F]

The condition for removing the protecting will depend on the protecting group being used. In certain embodiments, the invention provides a method of deprotecting the protected amine of a compound of formula:

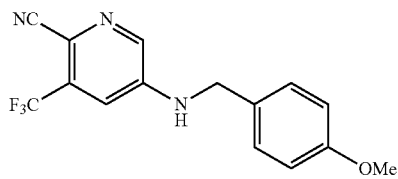 [SMILES: COc1ccc(CNc2cnc(Cl)c(C(F)(F)F)c2)cc1]

under suitable conditions to provide a compound of formula:

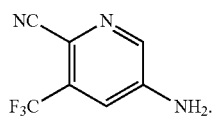

In certain embodiments, the deprotection is performed using trifluoroacetic acid. In certain embodiments, the solvent is methylene chloride. In certain embodiments, the deprotection reaction is performed at room temperature.

Synthesis of Eastern Portion

A new synthetic strategy for preparing eastern portion of A52 has also been developed. This new scheme has less steps and yields increased amounts of the final product B. 4-(1-cyanocyclobutylamino)-2-fluoro-N-methylbenzamide B or an analog thereof may be prepared using any of the strategies shown below.

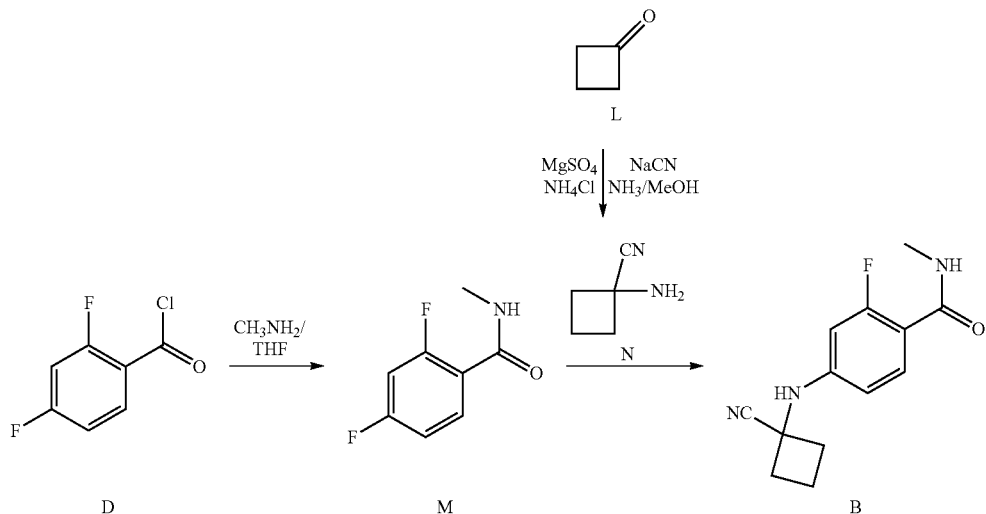
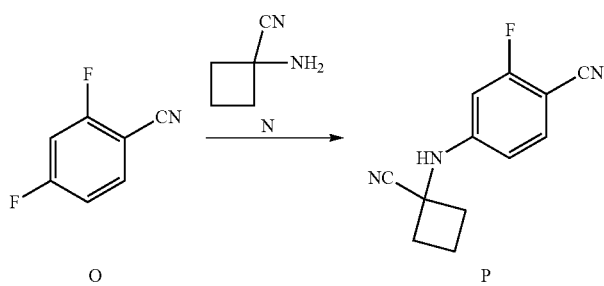
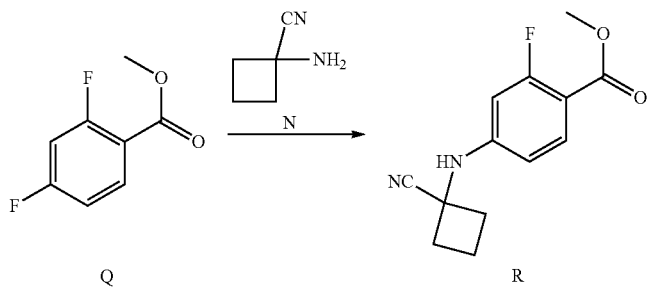
In certain embodiments, the ipso-substitution of the 4-fluoro moiety of the 2,4-difluorobenzyl amide M may be accomplished using 4-methoxybenzylamine or another protected amine as shown below. Simple deprotection of the amine followed by the Strecker reaction gave compound B.
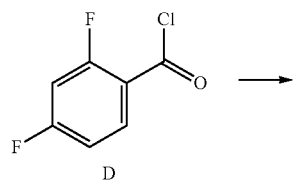

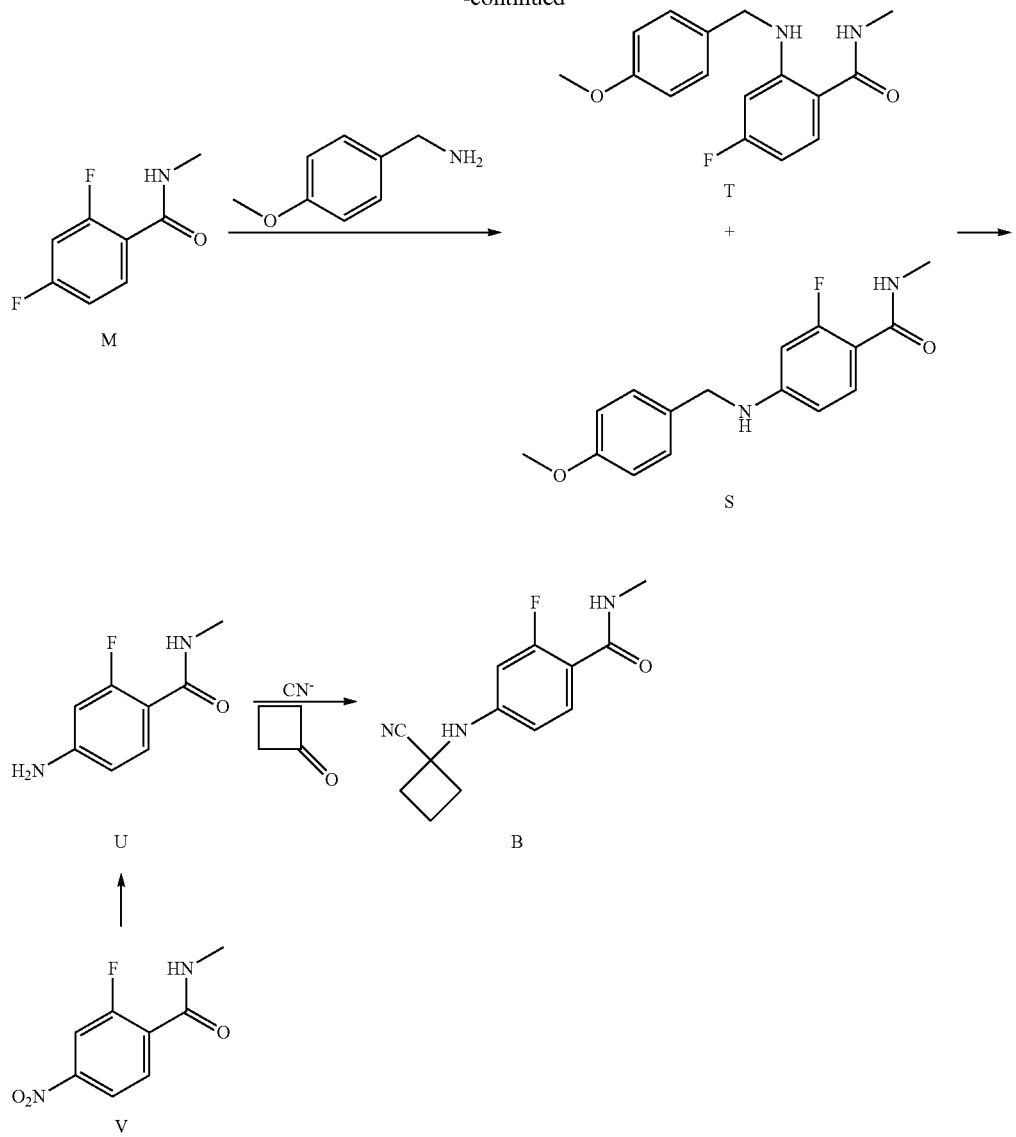
In certain embodiments, the method of synthesizing Compound B comprises the steps of:
(a) reacting a compound of formula:
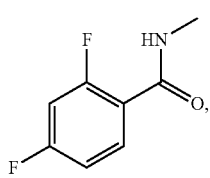
with an amine of formula:
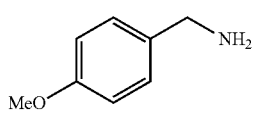
under suitable conditions to form a product of formula:
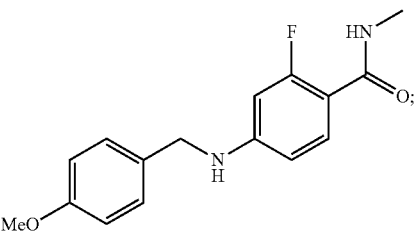

(b) deprotecting a compound of formula:

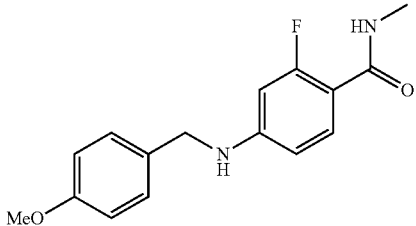 [SMILES: CNC(=O)c1ccc(NCc2ccc(OC)cc2)cc1F]

under suitable conditions to form a product of formula:

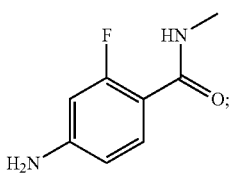

and (c) reacting a compound of formula:

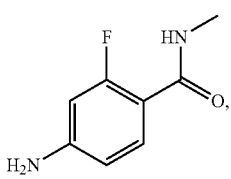

with

and a source of cyanide (CN) under suitable conditions to provide a compound of formula:

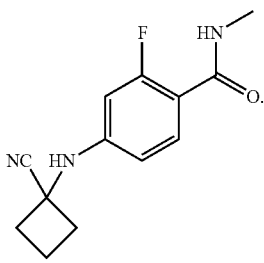 [SMILES: CNC(=O)c1ccc(NC2(C#N)CCC2)cc1F]

In certain embodiments, the invention provides a method of preparing the eastern portion of A52 comprising reacting a compound of formula:

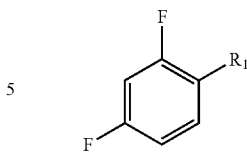

wherein $R_1$ is a substituted or unsubstituted acyl moiety or —CN, with

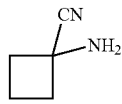

under suitable conditions to provide a compound of formula:

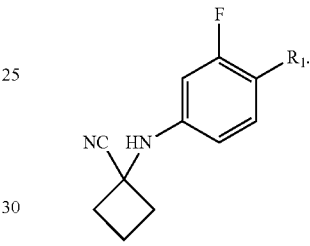

In certain embodiments, $R_1$ is acyl. In certain embodiments, $R_1$ is

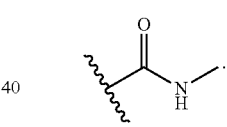

In certain embodiments, $R_1$ is

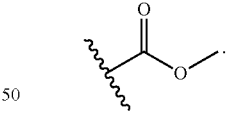

In certain embodiments, $R_1$ is —CN.

In certain embodiments, the method comprises reacting a compound of formula:

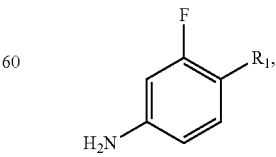

wherein $R_1$ is a substituted or unsubstituted acyl moiety or —CN, with

and a source of cyanide (CN) under suitable conditions to provide a compound of formula:

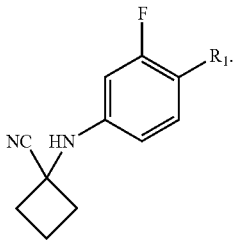

In certain embodiments, $R_1$ is acyl. In certain embodiments, $R_1$ is

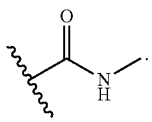 [SMILES: *C(=O)NC]

In certain embodiments, $R_1$ is

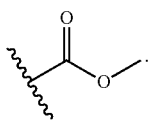 [SMILES: *C(=O)OC]

In certain embodiments, the source of cyanide is NaCN. In certain embodiments, the source of cyanide is KCN.

In certain embodiments, the method comprises reacting a compound of formula:

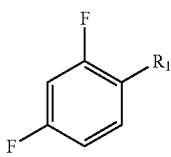

with a protected amine of formula:

wherein each PG is independently hydrogen or a suitable nitrogen-protecting group, under suitable conditions to form a product of formula:

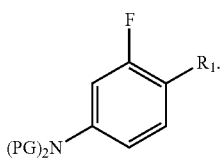

In certain embodiments, the method comprises reacting a compound of formula:

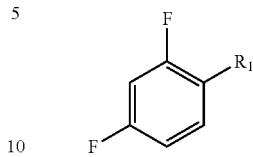

with an amine of formula:

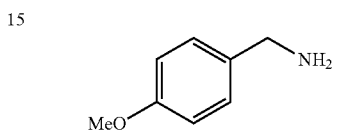

under suitable conditions to form a product of formula:

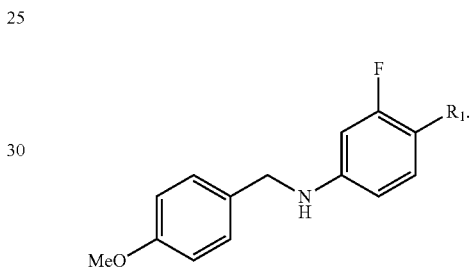

In certain embodiments, the reaction is carried out in DMSO as the solvent. In certain embodiments, the reaction mixture is irradiated with microwaves. In certain embodiments, the reaction mixture is heated to a temperature ranging from approximately 150° C. to approximately 200° C. In certain embodiments, the reaction mixture is heated to approximately 170° C. In certain embodiments, the reaction mixture is heated to approximately 180° C. In certain embodiments, the reaction mixture is heated to approximately 190° C. Preferably, the conditions of the reaction are such that the substitution of the amine occurs predominately at the 4-position rather than the 2-position of the phenyl ring.

In certain embodiments, the invention provides a method of deprotecting the amine. In certain embodiments, the method comprises deprotecting a compound of formula:

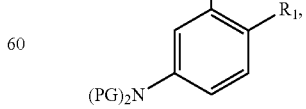

wherein each PG is independently hydrogen or a nitrogen-protecting group, under suitable conditions to form a product of formula:

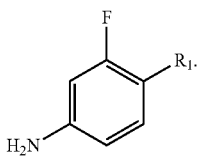

The conditions for removing the protecting group will depend on the protecting group being used. In certain particular embodiments, the method comprises deprotecting a compound of formula:

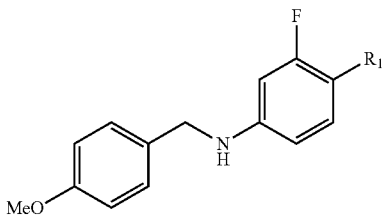

under suitable conditions to form a product of formula:

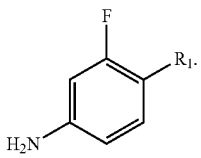

In certain embodiments, the deprotection step is done in the presence of trifluoroacetic acid. In certain embodiments, the deprotection step is done with trifluoroacetic acid in dichloromethane.

In certain embodiments, the method comprises reducing a compound of formula:

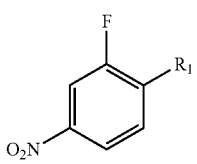

under suitable conditions to form a product of formula:

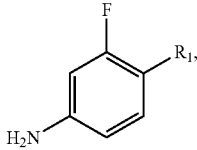

wherein $R_1$ is a substituted or unsubstituted acyl moiety or —CN. In certain embodiments, $R_1$ is acyl. In certain embodiments, $R_1$ is

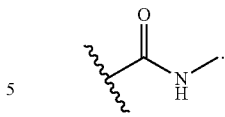

In certain embodiments, $R_1$ is

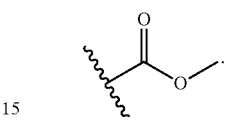

In certain embodiments, $R_1$ is —CN. This reduction of the nitro group is done in the presence of other functional groups which are susceptible to reduction. Preferably, the conditions of the reduction step are such that the nitro group is reduced without substantially affecting the other functional groups. In certain embodiments, the reduction is done with dissolved iron. In certain embodiments, the reduction is performed using iron powder (or other form of iron) dissolved in acetic acid (or other acid) and a solvent (e.g., ethyl acetate). In certain embodiments, at least 2 equivalents of iron are used. In certain embodiments, approximately 5 equivalents of iron are used. Other metals besides iron may also be used in this reduction step. In certain embodiments, the reaction is performed at room temperature. In certain embodiments, the reaction mixture is heated. In certain embodiments, the reaction is performed at approximately 60-75° C. In certain embodiments, the reaction is performed at approximately 65° C. In certain other embodiments, the reduction of the nitro group is performed using a Raney nickel hydrogenation. In certain embodiments, the nitro group is reduced to the corresponding amine in the presence of Raney nickel in ethanol (or other alcohol) at 50 psi $H_2$.

Formation of Thiohydantoin

Once the two halves of the desired compound are prepare, they are then coupled to form the resulting biarylthiohydantoin as shown below.

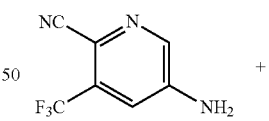

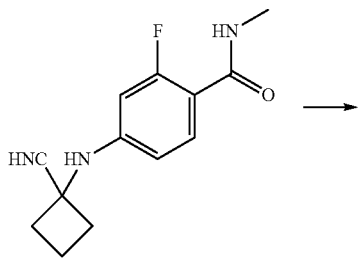

-continued

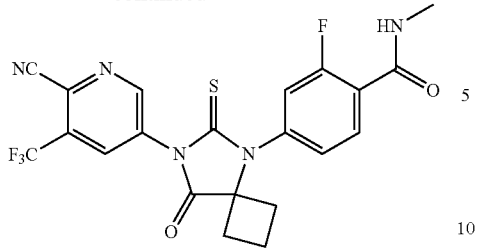

A52

In certain embodiments, the invention provides a method of synthesizing a biarylthiohydantoin of formula:

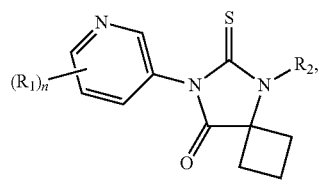

wherein n is an integer between 1 and 4, inclusive;

each $R_1$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_A$; —$C(=O)R_A$; —$CO_2R_A$; —CN; —SCN; —NCS; —$SR_A$; —$SOR_A$; —$SO_2R_A$; —$NO_2$; —$N_3$; —$N(R_A)_2$; —$NHC(=O)R_A$; —$NR_GC(=O)N(R_A)_2$; —$OC(=O)OR_A$; —$OC(=O)R_A$; —$OC(=O)N(R_A)_2$; —$NR_AC(=O)OR_A$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and $R_2$ is a substituted or unsubstituted aryl; or substituted or unsubstituted heteroaryl; comprising the step of coupling a substituted pyridine of formula:

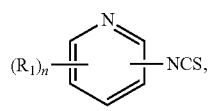

with a compound of formula:

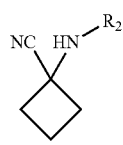

under suitable conditions to form a product of formula:

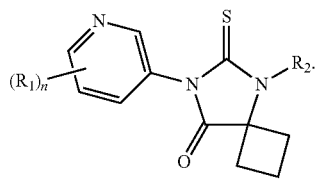

In certain embodiments, the step of coupling is performed with approximately 1 equivalent of each half of the molecule. In certain embodiments, the step of coupling is performed is with approximately 2-3 equivalents of the substituted pyridine and approximately 1 equivalent of the other half of the molecule. In certain embodiments, the coupling is performed in DMF at approximately 80° C. with microwave irradiation followed by acid hydrolysis (e.g., HCl in methanol) of the intermediate imidohydantoin. In certain embodiments, the coupling is performed by reacting the two halves of the molecule with thiophosgene, followed by heating in N,N-dimethylacetamide at about 60° C., and finally followed by acid hydrolysis (e.g., HCl in methanol) of the intermediate imidohydantoin. In certain embodiments, the final product is optionally purified. In certain embodiments, the final product is purified by column chromatography. In certain embodiments, the final product is purified by re-crystallization. In certain embodiments, the substituted pyridine is of the formula:

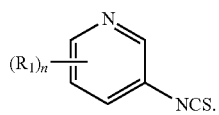

In certain embodiments, the compound for coupling of formula:

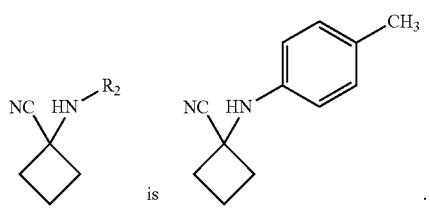

In certain embodiments, the compound for coupling of formula:

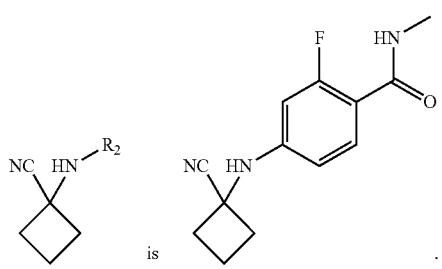

The inventive methodology allows for a scaleable synthesis of A52 and other analogs thereof. In certain embodiments, approximately 10 grams of the final product are prepared using the inventive synthesis. In certain embodiments, approximately 20 grams of the final product are prepared. In certain embodiments, approximately 50 grams of the final product are prepared. In certain embodiments, approximately 100 grams of the final product are prepared. In certain embodiments, approximately 200 grams of the final product are prepared. In certain embodiments, approximately 500 grams of the final product are prepared. In certain embodiments, approximately 1000 grams of the final product are prepared. The inventive synthesis also provides compound that is at least 90%, 95%, 98%, 99%, or 99.9% pure. In certain embodiments, the synthesis provides a compound that is sufficiently pure that it could be formulated and administered to humans or other animals. In certain embodiments, the resulting compound is used in veterinary medicine. In certain embodiments, the resulting compound is used for pre-clinical studies.

Intermediates

Not only does the invention provide methodology for preparing biarylthiohydantions, but it also provides useful intermediates as well.

In certain embodiments, the invention provides a compound of formula:

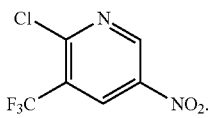

In certain embodiments, the invention provides a compound of formula:

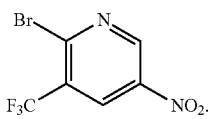

In certain embodiments, the invention provides a compound of formula:

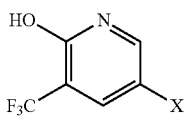

wherein X is a halogen. In certain embodiments, X is bromine. In certain embodiments, X is iodine.

In certain embodiments, the invention provides a compound of formula:

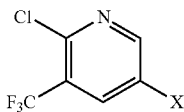

wherein X is halogen. In certain embodiments, X is bromine. In certain embodiments, X is iodine.

In certain embodiments, the invention provides a compound of formula:

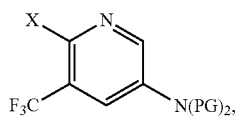

wherein X is halogen or —CN; and each PG is independently hydrogen or a nitrogen protecting group. In certain embodiments, X is chlorine. In certain embodiments, X is bromine. In certain embodiments, X is iodine. In certain embodiments, X is —CN. In certain embodiments, at least one PG is hydrogen. In certain embodiments, PG is benzyl. In certain embodiments, PG is methoxybenzyl. In certain embodiments, PG is 4-methoxybenzyl.

In certain embodiments, the invention provides a compound of formula:

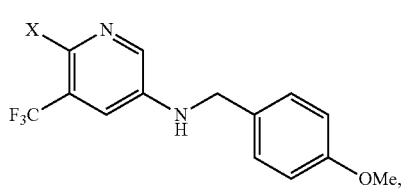

wherein X is halogen or —CN. In certain embodiments, X is chlorine. In certain embodiments, X is bromine. In certain embodiments, X is iodine. In certain embodiments, X is —CN.

In certain embodiments, the invention provides a compound of formula:

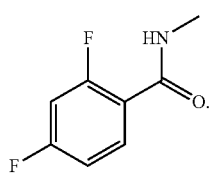

In certain embodiments, the invention provides a compound of formula:

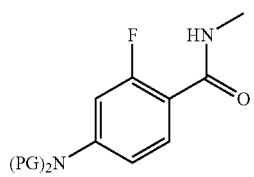

wherein each PG is independently hydrogen or a nitrogen protecting group. In certain embodiments, the invention provides a compound of formula:

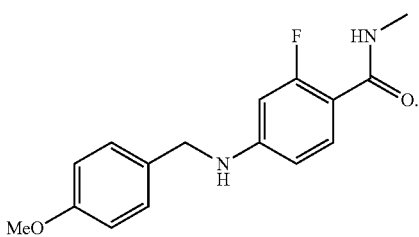 [SMILES: CNC(=O)c1ccc(NCc2ccc(OC)cc2)cc1F]

In certain embodiments, the invention provides a compound of formula:

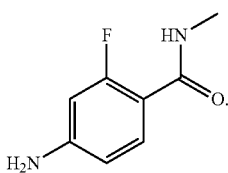

In certain embodiments, the invention provides a compound of formula:

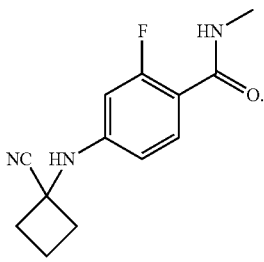 [SMILES: CNC(=O)c1ccc(NC2(C#N)CCC2)cc1F]

These and other aspects of the present invention will be further appreciated upon consideration of the following Examples, which are intended to illustrate certain particular embodiments of the invention but are not intended to limit its scope, as defined by the claims.

EXAMPLES

Example 1—Synthesis of A52

This example provides an alternative route to the two key intermediates, namely 3-(trifluoromethyl)-5-isothiocyanato-pyridine-2-carbonitrile A and 4-(1-cyano-1-cyclobuty-lamino)-2-fluoro-N-methylbenzamide B, as shown in the retrosynthetic analysis in FIG. 1.

The route described below provides compound A through a shorter sequence of steps from nitropyridone E (Scheme 1 below) by selective reduction of the nitro group using dissolved iron followed by palladium-catalyzed cyanation. The synthesis of intermediate A was further improved via the sequence of steps entailing chlorination of the 5-nitro-pyridine E, palladium-catalyzed cyanation (Chobanian et al., *Tetrahedron Letters*, 2006, 47, 3303-3305) at carbon 2 to give G, and subsequent selective reduction of the nitro group to the corresponding amine (Salvati, et al., Published US Patent Application, 2004/077605, which is incorporated herein by reference), in the presence of the very active nitrile, using dissolving iron in acetic acid to lead to amine H in a good yield. Finally, the conversion of the amine to the corresponding isothiocyanate with thiophosgene in the presence of base concluded the synthesis of the western half of A52.

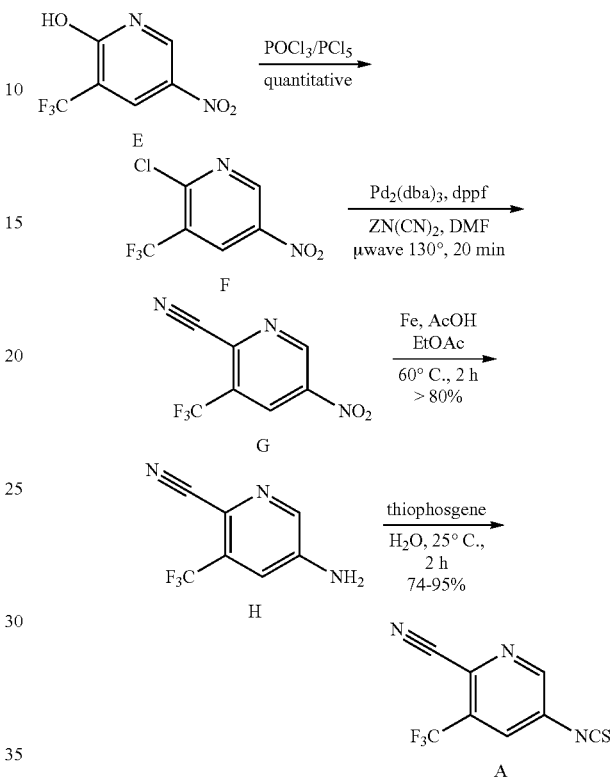

Scheme 1. Synthesis of western half of A52, Isothiocyanate A

While the method above has shortened the synthesis by four steps, as well as provided a better overall yield, another route was sought to avoid nitration by providing a more accessible precursor to the amino group. More reactive derivatives of C, such as 5-iodo-3-trifluoro-2-pyridone I or the respective 5-bromo were considered as preferred precursors to provide an anchoring position for the amine in H. The amine at carbon 5 of H could be the result of the displacement of a bromide, triflate, iodide, or the like directly through nucleophilic aromatic substitution and/or through transition metal catalyzed amination, alkyl amination, or carbamoyaltion. The amine could be a free one such as ammonia, or in a protected form such that the protecting group could be later removed to provide the desired amine. Protecting groups of the amine could be chosen among those that are removable by hydrogenolysis such as benzyl amine and its electron-rich analogs such as methoxybenzylamine, preferably 4-methoxybenzylamine. Another set of protected amines that are known to react in a transition metal catalyzed coupling are active amides, carbamates, and amines that are released through the action of fluoride ion on a silyl or silylalkyl amine. Exemplary carbamates useful in the invention are tertiobutylcabamate and benzylcarbamate. They react with iodopyridone under palladium-mediated catalysis.

Compound H is accessed through the following sequence of steps: iodination of 3-triluoromethyl-2-pyridone C, chlorination of resulting pyridone to the respective 2-chloropyridine J, two successive Pd-catalyzed substitutions, the first of which at position 5 on the iodide by a protected amine, and the second at position 2 which introduces the required cyano group; and lastly the removal of the protecting group on the amine by trifluoroacetic acid, and formation of the corresponding thiocyanate. While longer than previous schemes, this embodiment proved to be better at scaling up while requiring smaller amounts of catalyst and providing better yields of the desired final product.

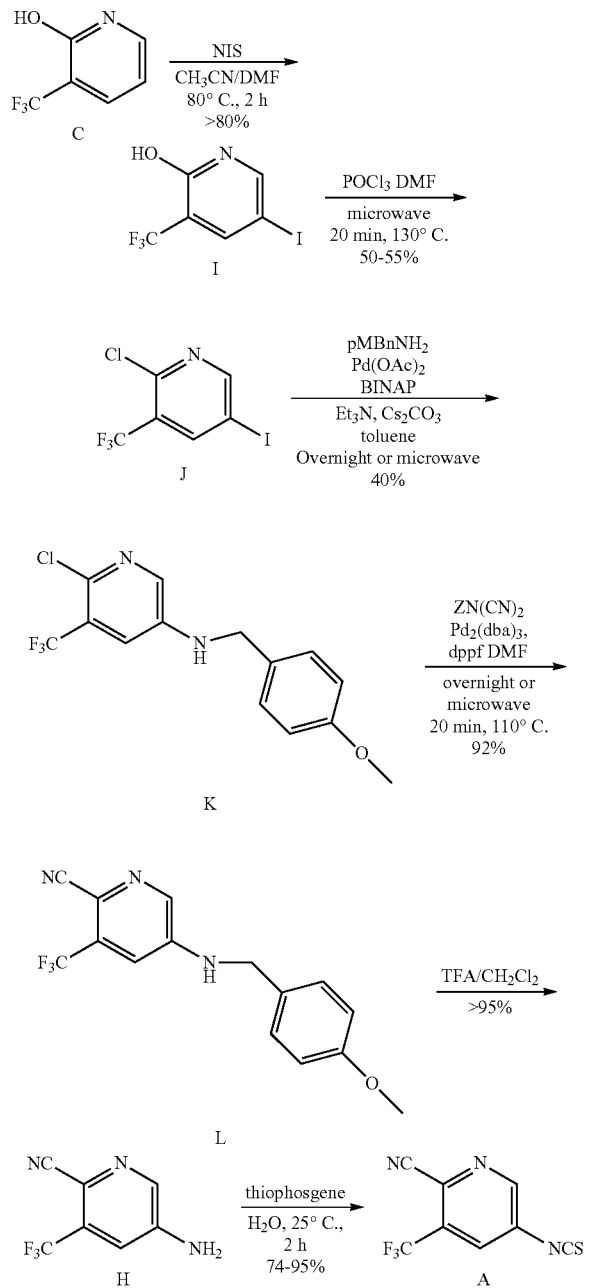

The iodination was performed following a described procedure (R. Kawai, M. Kimoto, S. Ikeda, T. Mitsui, M. Endo, S. Yokoyama and I. Hirao, *J. Am Chem Soc*, 2005, 127, 17286-17295) to provide compound I. Then a slight modification of a published method (S. Kagabu, *Synthetic Communications*, 2006, 36, 1235-1245) was used to access chloro-iodopyridine intermediate J. Microwave irradiation was used which shortens the reaction time from four hours to 20 min. Subsequently, a first transition metal assisted coupling (J. Kuethe, A. Wong, and I. W. Davies, *J. Org. Chem.*, 2004, 69, 7752-7754) using only 3 mol % of the palladium acetate catalyst involving the position 5 of the pyridinium ring activated with an iodide led to intermediate K. The latter, in turn, undergoes a palladium-assisted cyanation as previously executed in Scheme 2, to provide the intermediate L with yields averaging 90%. Finally simple deprotection of the amine with concentrated trifluoroacetic acid gave H in quantitative yield. The conversion of the amine to the isothiocyanate with thiophosgene concludes the preparation of the intermediate A.

Using Pd$_2$(dba)$_3$ and xantphos ligand in the presence of sodium tertiobutoxide under refluxing toluene, selective substitution at the iodide site could be achieved in scaleable yields that are greater than 85% (Scheme 3).

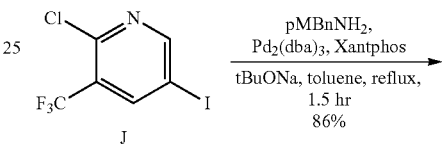

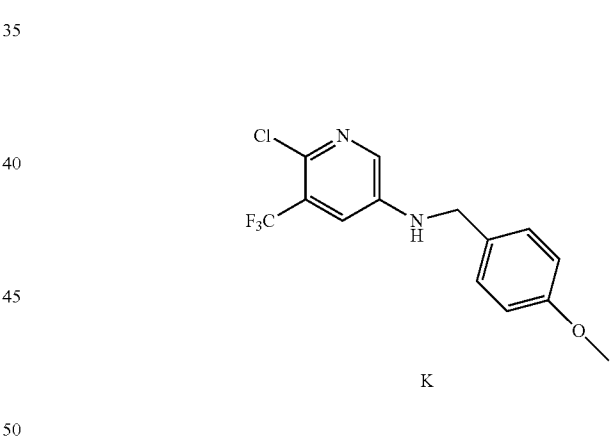

Improved Synthesis of the Right Half of A52, Intermediate B

A new synthesis of the right half of A52 has also been developed, namely a new method to prepare 4-(1-cyanocyclobutylamino)-2-fluoro-N-methylbenzamide (B), with a shorter number of steps and that provides increased amounts of B. As shown in Scheme 4, the fluorine atom in para-fluorobenzonitrile O is displaced by the not so nucleophilic amine N namely 1-amino-1-cyanocyclobutane. But, due to the presence of an additional nitrile in the final intermediate B, it should be possible and preferable to displace the fluorine atom on the methyl 2,4-difuorobenzoic ester Q. However, methyl 2,4-difluorobenzyl amide M though less active under the reaction conditions should provide a more direct access and also ease the follow up functional modifications to reach N-methyl amide B.

Scheme 4

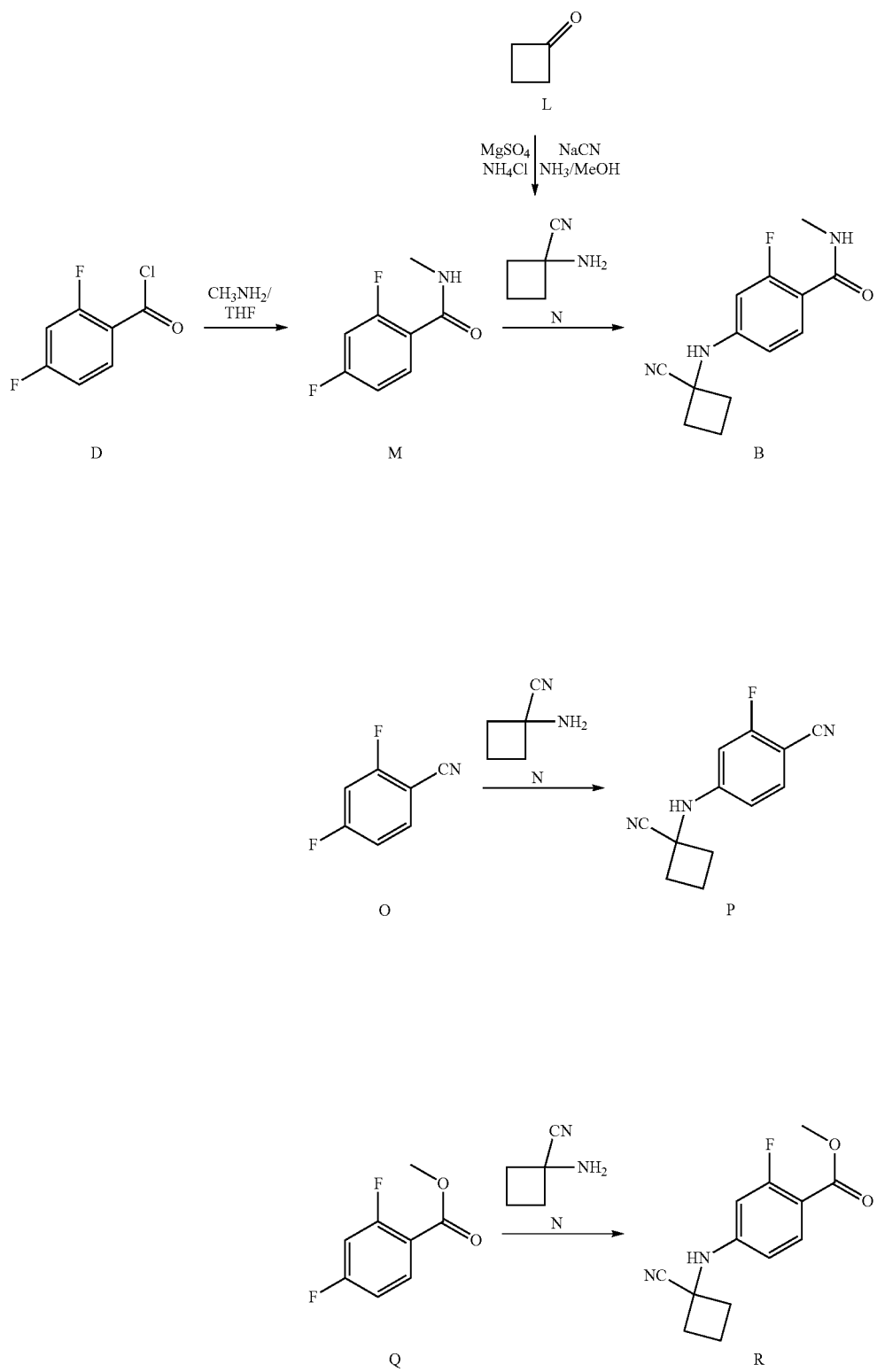

Considering all these reactivity patterns, a route for the preparation of B in large amounts has been achieved (Scheme 5). By applying microwave assistance, effective ipso-substitution of the 4-fluoride in 2,4-difluorobenzyl amide M with para-methoxybenzylamine provided the amide S in about 20% yield (un-optimized). Simple deprotection of the amine and Strecker reaction with cyclobutanone gave key intermediate B.

Scheme 5. Route to 4-(1-cyanocyclobutylamino)-2-fluoro-N-methylbenzamide (B)
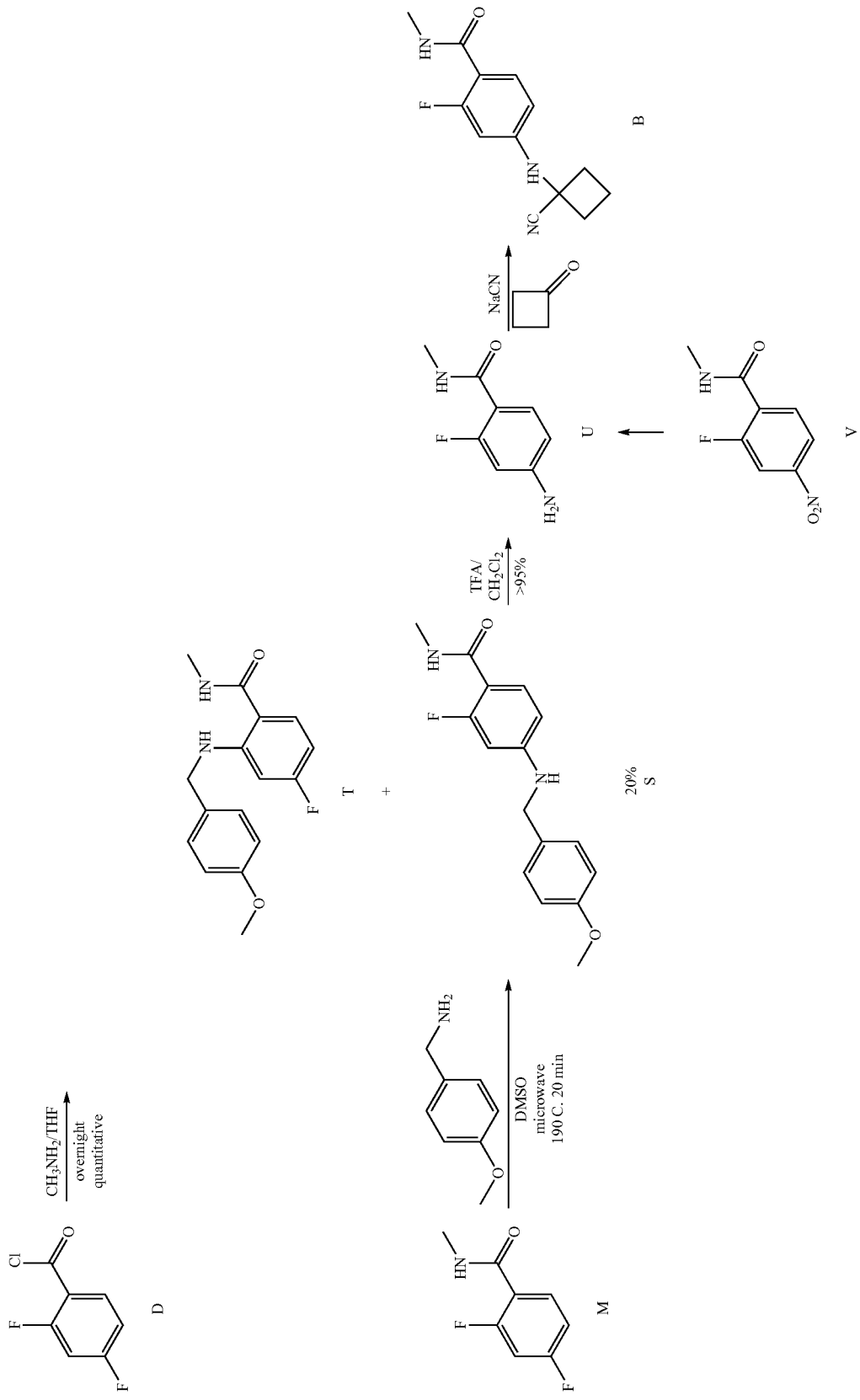

Convergent Coupling to Yield A52

The final coupling step between intermediates A and B is achieved by microwave irradiation and cyclization to the biarylthiohydantoin A52 (Scheme 6). Although 3 equivalents of A are required for the highest yields in this transformation, the un-reacted amine A can be recovered.

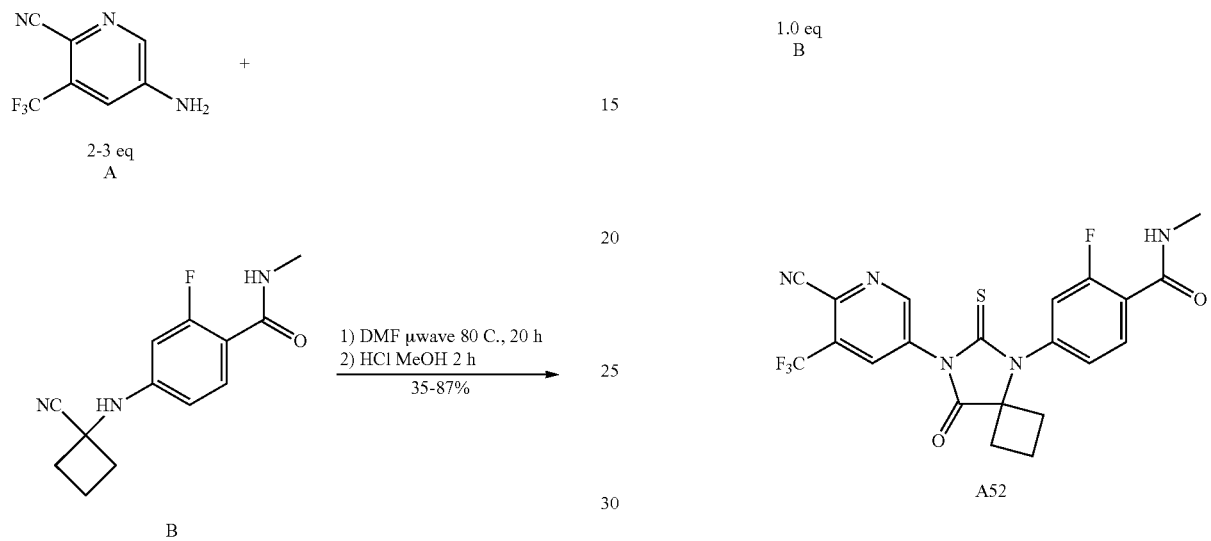

Scheme 6. Final coupling of intermediates A and B to give A52.

Another method to access A52 uses a different solvent at lower temperature, but for a longer reaction time. Indeed, when 1.05 molar equivalents of amine A and 1.0 equivalent of amide B were mixed in N,N-dimethylacetamide, and the resulting mixture brought to 60° C. for 6 to 14 hours, followed by acid hydrolysis of the intermediate imidohydantoin, A52 could be isolated in yields that are greater than 75% (Scheme 7).

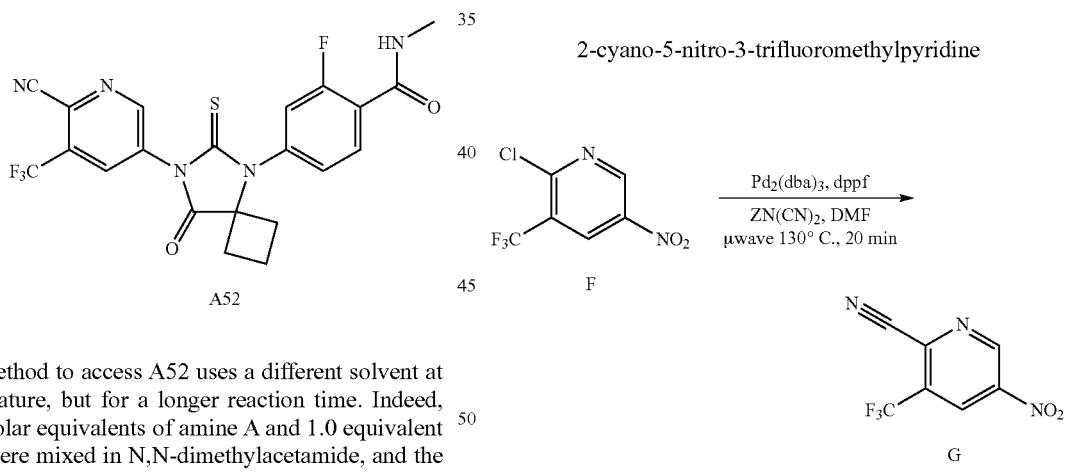

Scheme 7

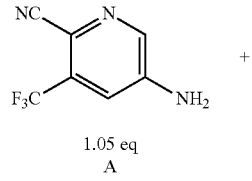

Experimental Section

2-cyano-5-nitro-3-trifluoromethylpyridine

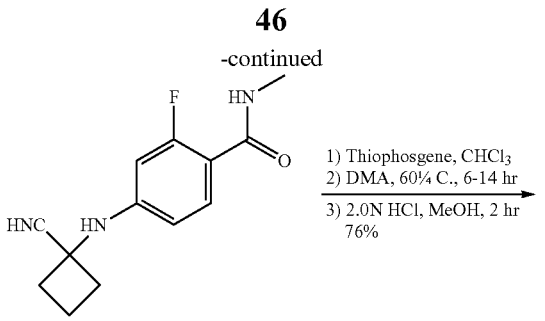

Zinc cyanide (25 mg, 0.216 mmol, 1.2 eq) is added to the chloride (43 mg, 0.180 mmol) solubilized in DMF (1 ml). The solution is degassed for 10 minutes. Then the ligand dppf (20 mg, 0.036 mmol, 0.2 eq) is added. The solution is degassed again for 5 min. The catalyst Pd$_2$(dba)$_3$ (25 mg, 0.027 mmol, 0.15 eq) is added, the solution is degassed for 5 more minutes. The reaction mixture is then heated at 130° C. for 20 min in a microwave. After filtration, the solvent is evaporated and the crude residue is purified by flash chromatography on silica gel (hexane/EtOAc) to afford 16 mg (40%) of the desired product.

$^1$H NMR (400 MHz, CDCl$_3$) δ 8.60 (d, J=2.5, 1H); 9.08 (d, J=2.5, 1H),

5-amino-2-cyano-3-trifluoromethylpyridine

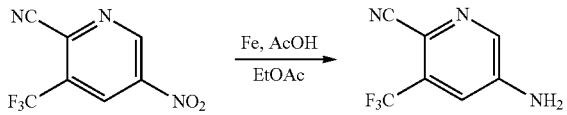 [SMILES: "EtOAc" ; N#Cc1ncc([N+](=O)[O-])cc1C(F)(F)F ; N#Cc1ncc(N)cc1C(F)(F)F]

2-cyano-5-nitro-3-trifluoromethylpyridine (7 mg, 0.032 mmol) is dissolved in 1:1 EtOAc/AcOH (1 mL) and heated to 65° C. Iron powder (9 mg, 0.161 μmol, 5 eq, 325 mesh) is added and the mixture stirred for 2 hours. The mixture is filtered through celite, and the filtrate is concentrated under vacuo. The crude residue is purified by flash chromatography on silica gel (hexane/EtOAc) to afford 4 mg (67%) of the desired product.

$^1$H NMR (400 MHz CDCl3) δ 7.20 (d, J=2.4 Hz, 1H), 8.22 (d, J=2.4 Hz, 1H).

5-iodo-3-trifluoromethyl-2-pyridinol

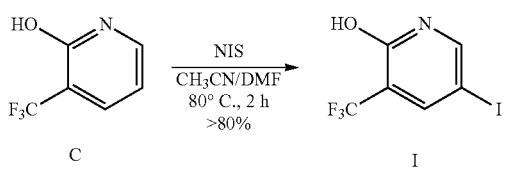

3-trifluoromethyl-2-pyridinol (25 g, 153.3 mmol) is dissolved in anhydrous CH$_3$CN (150 mL) and DMF (150 mL). N-iodosuccinimide (34.5 g, 153 mmol) is then added. The reaction mixture is stirred at 80° C. for 2 hours and cooled to room temperature. Aqueous 1 M NaHCO$_3$ (150 mL) is then added to the cooled mixture. After stirring for 5 min, the solvents are evaporated to dryness. Water is added and the aqueous phase is extracted (x2) with dichloromethane. The organic phase is then evaporated and the desired product is recrystallized in water to afford 36.2 g (81%) of a white powder.

$^1$H NMR (500 MHz, CDCl$_3$) δ 7.85 (d, J=2.3, 1H); 7.98 (d, J=2.3, 1H), 13.41 (br s, 1H); $^{13}$C NMR (250 MHz CDCl$_3$) δ 63.0, 121.4 (q, J$_{C-F}$=272.3 Hz), 122.2 (q, J$_{C-F}$=31.6 Hz), 144.4, 148.1 q, (J$_{C-F}$=5.0 Hz), 160.1.

2-choro-5-iodo-3-trifluoromethylpyridine

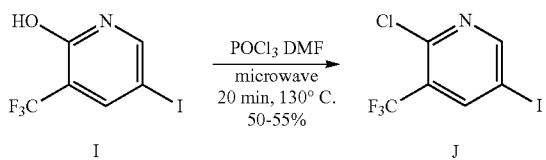

To an ice-cold mixture of POCl$_3$ (1.60 mL) and DMF (1 mL) in a microwave vial, 5-iodo-3-trifluoromethyl-2-pyridinol (1 g, 3.47 mmol) is added. The vial is sealed and heated 20 min at 110° C. The reaction mixture cooled at room temperature is poured into ice cold water. The product precipitates. The precipitate is filtered, washed with cold water and dried to afford 661 mg (62%) of a light brown powder.

$^1$H NMR (500 MHz CDCl$_3$) δ 8.32 (d, J=2.0 Hz, 1H), 8.81 (d, J=2.0 Hz, 1H). $^{13}$C NMR (250 MHz CDCl$_3$) δ 89.4, 121.2 (q, J$_{C-F}$=273.3 Hz), 126.8 (q, J$_{C-F}$=33.6 Hz), 144.34, 148.5, 158.7.

2-choro-3-trifluoromethyl-N-paramethoxybenzylpyridin-5-amine K

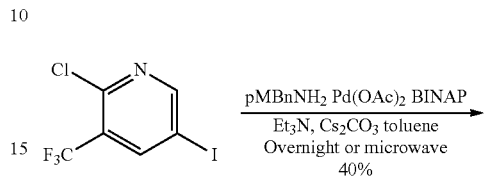

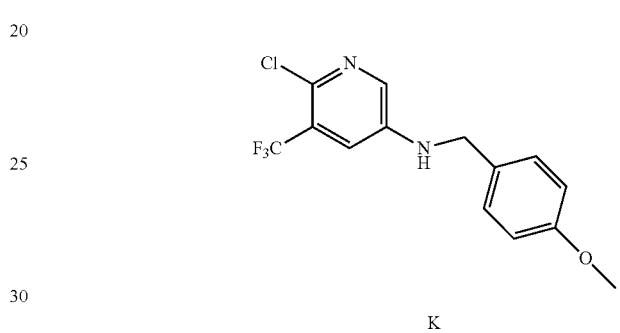

2-choro-5-iodo-3-trifluoromethylpyridine is dried under vacuum. To a slurry of chloroiodpyridine (10 g, 32.6 mmol) in toluene (anhydrous) (98 mL) is added sequentially. Pd(OAc)$_2$ (220 mg, 0.98 mmol, 0.03 eq), rac-BINAP (609 mg, 0.98 mmol, 0.03 eq) solid Cs$_2$CO$_3$ (53 g, 163 mmol, 5 eq), paramethoxybenzylamine (4.05 mL, 30.9 mmol, 0.95 eq) and triethylamine (0.41 mL, 2.93 mmol, 0.09 eq). The resulting slurry is degassed (x2) by vacuum/Argon backfills. The mixture is heated to reflux overnight. The mixture is then cooled to room temperature and H$_2$O is added. The layers are separated and the toluene layer is concentrated under vacuo. The residue is purified by flash chromatography on silica gel (Hexane/EtOac; 95:5 to 30/70) to afford 4 g of white solid desired compound (40%).

$^1$H NMR (500 MHz CDCl$_3$) δ 3.81 (s, 3H), 4.29 (d, J=5.1 Hz, 2H), 4.32 (br s, 1H), 6.90 (d, J=8.1 Hz, 2H), 7.19 (d, J=2.9 Hz, 1H), 7.26 (d, J=8.1 Hz, 2H), 7.92 (d, J=2.9 Hz, 1H). $^{13}$C NMR (250 MHz CDCl$_3$) δ 47.3, 55.4, 114.3, 119.3 (q, J$_{C-F}$=5.1 Hz), 122.3 (q, J$_{C-F}$=272.9 Hz), 124.80 (q, J$_{C-F}$=32.7 Hz), 128.8, 129.1, 135.1, 136.6, 142.9, 159.3.

Alternative Synthesis of Intermediate K

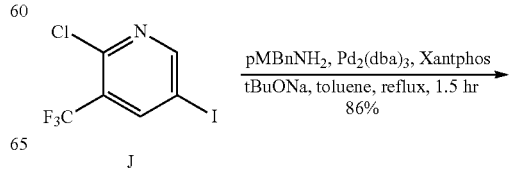

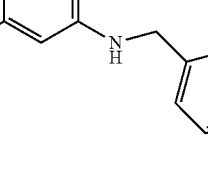

K

A suspension of vacuum dried 2-choro-5-iodo-3-trifluoromethylpyridine (50 g, 163 mmol) in anhydrous toluene (1,500 mL) was treated sequentially with $Pd_2(dba)_3$ (2.98 g, 3.25 mmol, 0.02 eq), Xantphos (5.65 g, 9.76 mmol, 0.06 eq), solid t-BuONa (23.4 g, 243 mmol, 1.5 eq), and paramethoxybenzylamine (23.2 mL, 179 mmol, 1.1 eq). The resulting slurry is degassed by vacuum/argon backfills for 10 min. The mixture is then quickly brought to reflux by a pre-heated oil bath. After 1.5 hours at this temperature, the mixture was cooled to the ambient, and the solids were removed by filtration over a packed bed of celite and washed with toluene. The filtrate was then diluted with EtOAc (200 mL), then washed with $H_2O$. The organic layer was concentrated under reduced pressure gave an oily solid. Crystallization from DCM/Hexane gave (36.6 g, 71%) of B as a light yellow solid.

Alternatively, smaller scales (5 to 10 gr of A) were purified by column silica gel chromatography using the gradient system Hexane-EtOAc 19-1 to 3-7 (v-v). This gave yields in excess of 85% of B as a white solid.

2-cyano-3-trifluoromethyl-N-paramethoxybenzylpyridin-5-amine

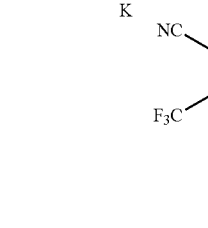

0.32 mmol, 0.1 eq) is added, the solution is degassed for 5 more minutes. The reaction mixture is then heated at 150° C. for 10 min. After filtration, the solvent is evaporated and the crude residue is purified by flash chromatography on silica gel (hexane/EtOAc) to afford 900 mg (93%) of a dark yellow oil.

$^1$H NMR (500 MHz CDCl3) δ 3.82 (s, 3H), 4.37 (d, J=5.3 Hz, 2H), 4.93 (br s, 1H), 6.92 (d, J=9.5, 2H), 7.08 (d, J=2.7 Hz, 1H), 7.25 (d, J=9.5, 2H), 8.17 (d, J=2.7 Hz, 1H). $^{13}$C NMR (250 MHz CDCl3) δ 46.7, 55.4, 113.9, 114.5, 115.9, 116.1, 122.0 (q, $J_{C-F}$=274.5 Hz), 128.0, 128.9, 131.4 (q, $J_{C-F}$=33.1 Hz), 138.68, 145.9, 159.5.

5-amino-2-cyano-3-trifluoromethylpyridine H

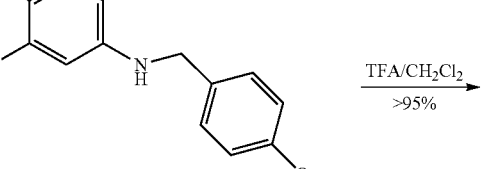

TFA (1 mL) is added dropwise to a solution of pyridine L (83 mg, 0.27 mmol) in dry DCM (0.5 mL) under argon. The solution is stirred overnight at room temperature. After completion of the reaction, the solvent is evaporated and the residue is purified by flash chromatography on silica gel (Hexane/EtOac) to afford the desired product quantitatively.

$^1$H NMR (500 MHz CDCl3) δ 7.20 (d, J=2.4 Hz, 1H), 8.22 (d, J=2.4 Hz, 1H).

Scale Up and Purification of H

For the larger scales, an improved process calls for dissolving pyridine L (53 g, 0.172 mol) in TFA/DCM (170 mL, 4:1) at room temperature. Upon reaction completion (approximately 2 hours at room temperature), the volatiles were removed under reduced pressure. The residue is then diluted with EtOAc (800 mL), and washed with saturated aqueous $NaHCO_3$. Vacuum concentration and precipitation from DCM-Hexane (1-2, v-v) gave a relatively clean product. Further washing with DCM gave pure intermediate H as a white solid (27.43 g, 85%).

Methyl 2,4-difluorobenzylamide

Zinc cyanide (0.45 g, 3.80 mmol, 1.2 eq) is added to the chloride (1 g, 3.16 mmol) solubilized in DMF (20 ml). The solution is degassed for 10 minutes. Then the ligand dppf (0.35 g, 0.63 mmol, 0.2 eq) is added. The solution is degassed again for 5 min. The catalyst $Pd_2(dba)_3$ (0.29 g,

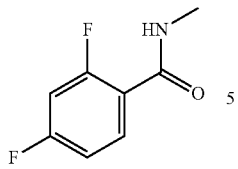

Methylamine 2M in THF (12.4 mL, 1.1 eq) is added to neat 2,4-difluorobenzoyl chloride (4 g, 22.6 mmol). The reaction mixture is stirred overnight at room temperature. The solvent is evaporated, ethyl acetate is added to solubilize the residue. The organic is washed with aqueous NaHCO₃, dried with Na₂SO₄, filtered and evaporated to afford the quantitatively the desired compound as a white powder.

¹H NMR (500 MHz CDCl3) δ 3.00 (d, J=4.8 Hz, 3H), 6.84 (m, J=2.3; 10.3 Hz, 1H), 6.97 (m, J=2.3; 8.2 Hz, 1H), 8.08 (td, J=6.8; 8.9 Hz, 1H) ¹³C NMR (100 MHz CDCl3) δ 27.0, 104.3 (d, J=26.0 Hz), 104.6 (d, J=25.9 Hz), 112.4 (dd, J=21.2; 3.1 Hz), 118.1 (dd, J=12.4; 3.8 Hz), 133.7 (dd, J=10.1; 3.9 Hz), 162.9 (dd, J=381.1; 12.3 Hz), 163.5.

Methyl 2-fluoro-4-paramethoxybenzylamine-benzylamide

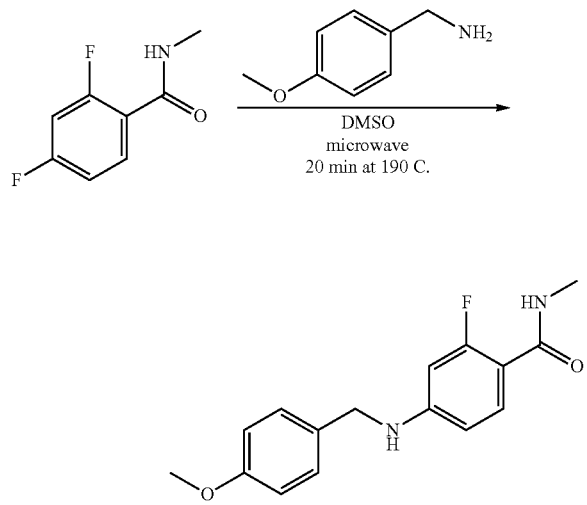

Paramethoxybenzylamine (0.069 mL, 0.548 mmol, 2 eq) is added to methyl 2,4-difluorobenzylamide (47 mg, 0.274 mmol) dissolved in dimethylsulfoxide (0.5 mL). The reaction mixture is heated at 190° C. for 20 min in a microwave. After completion the solvent is evaporated and the residue is purified by flash chromatography on silica gel (hexane/ethyl acetate) to give 18 mg (20%) of the desired product.

¹H NMR (500 MHz CDCl3) δ 2.98 (d, J=4.5 Hz, 3H), 3.81 (s, 3H), 4.26 (d, J=5.3 Hz, 2H), 4.47 (br s, 1H), 6.23 (dd, J=2.2; 15.1 Hz, 1H), 6.45 (dd, J=2.2; 8.7 Hz, 1H), 6.58 (br s, 1H), 6.89 (d, J=8.7 Hz, 2H), 7.25 (d, J=8.7 Hz, 2H), 7.91 (t, J=9.0 Hz, 1H). ¹³C NMR (500 MHz CDCl3) δ 26.6, 47.3, 55.3, 98.2 (d, J=29.7 Hz), 109.25, 114.4, 128.6, 129.9, 133.1 (d, J=4.5 Hz), 152.3 (d, J=12.5 Hz), 159.1, 161.5, 163.9 (d, J=244 Hz), 164.5.

Methyl 4-amino-2-fluoro-benzylamide

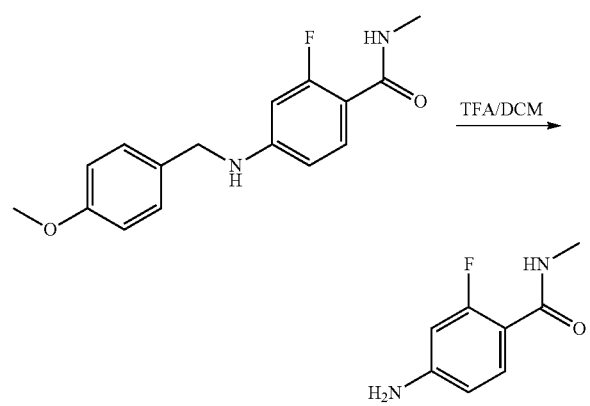

TFA (1 mL) is added dropwise to a solution of methylamide (60 mg, 0.21 mmol) in dry DCM (0.5 mL) under argon. The solution is stirred overnight at room temperature. After completion of the reaction, the solvent is evaporated and the residue is purified by flash chromatography on silica gel (Hexane/EtOac) to afford the desired product quantitatively.

¹H NMR (500 MHz CDCl3) δ 2.98 (d, J=4.8 Hz, 3H), 4.15 (br s, 2H), 6.32 (d, J=14.3 Hz, 1H), 6.48 (d, J=8.2 Hz, 1H), 6.61 (br s, 1H), 7.90 (dd, J=8.6 Hz, 1H), ¹³C NMR (500 MHz CDCl3) δ 26.63, 100.8 (d, J=28.8 Hz), 110.3 (d, J=244.6 Hz), 110.9, 133.3 (d, J=4.3 Hz), 151.4 (d, J=12.5 Hz), 162.2 (d, J=244.6 Hz), 164.3 (d, J=3.5 Hz).

Synthesis of N-methyl-4-[7-(6-cyano-5-trifluoromethylpyridin-2-yl)-8-oxo-6-thioxo-5,7-diazaspiro[3.4]octan-5-yl]-2-fluorobenzamide (A52)

One Pot Small Scale (2.8 gr) Thiohydantoin Formation in DMF

Thiophosgene (1.2 mL, 1.16 eq, 15.6 mmol) is added dropwise to a solution of 5-amino-2-cyano-3-trifluoromethylpyridine (2.8 g, 1.1 eq, 15.0 mmol) and N-methyl-4-(1-cyanocyclobutylamino)-2-fluorobenzamide (3.35 g, 13.5 mmol) in dry DMF (25 mL) under Argon. The solution is stirred overnight at 60° C. To this mixture were added MeOH (60 mL) and aq. 2M HCl (30 mL), then the mixture was reflux for 2 h. After cooling to rt, the mixture was poured into ice water (100 mL) and extracted with EtOAc (3×60 mL). The organic layer was dried over Mg₂SO₄, concentrated and chromatographed on silica gel using 5% acetone in DCM to yield the desired product (2.65 g, 41%).

Alternative Synthesis of A52

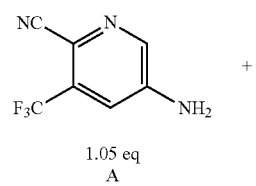

1.05 eq
A

-continued

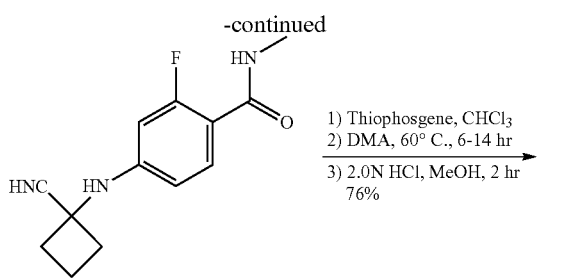

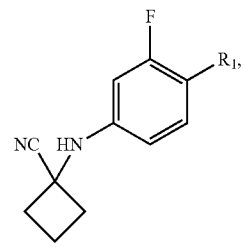

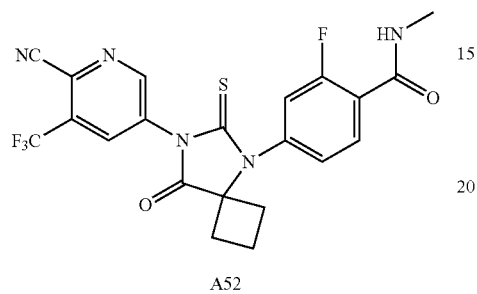

A52

Thiophosgene (1.23 mL, 16.0 mmol) is added dropwise to a solution of 5-amino-2-cyano-3-trifluoromethylpyridine (3.0 g, 16.0 mmol) and N-methyl-4-(1-cyanocyclobutylamino)-2-fluorobenzamide (3.96 g, 16.0 mmol) in dry DMA (35 mL) under Argon. The solution is stirred overnight at 60° C. To this mixture were added MeOH (60 mL) and aq. 2M HCl (30 mL), then it was brought to reflux temperature for 2 h. After cooling down to the ambient, the mixture was poured into ice water (100 mL) and extracted with EtOAc (3×60 mL). The organic layer was dried over Mg$_2$SO$_4$, filtered over celite, and concentrated under reduced pressure. Silica gel chromatography using DCM/-acetone 19-1 (v-v) yielded the desired product (5.78 g, 76%).

Scale Up.

Thiophosgene (5.48 mL, 1.05 eq, 70.9 mmol) is added dropwise to a solution of 5-amino-2-cyano-3-trifluoromethylpyridine (13.27 g, 1.05 eq, 70.9 mmol) and N-methyl-4-(1-cyanocyclobutylamino)-2-fluorobenzamide (16.7 g, 67.5 mmol) in dry DMA (110 mL) under Argon at 0° C. After 10 min, the solution was heated up to 60° C. and allowed to stir at that temperature for an overnight period. This was then diluted with MeOH (200 mL) and treated with aq. 2M HCl (140 mL), then the mixture was refluxed for 2 h. After cooling down to RT, the mixture was poured into ice water (500 mL), and filtered over buchner. The solid was recrystallized from DCM/EtOH to get desired product (20.6 g, 64%).

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method of synthesizing a compound of formula:

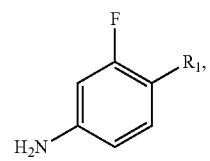

the method comprising:
reacting a compound of formula:

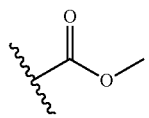 [SMILES: *C(=O)OC]

wherein R$_1$ is

or —CN, with

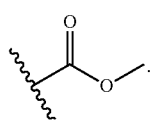 [SMILES: *C(=O)OC]

in the presence of a source of cyanide to provide a compound of formula:

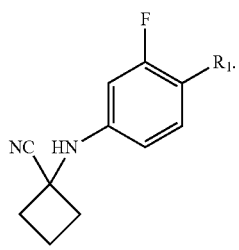

2. The method of claim 1, wherein R$_1$ is

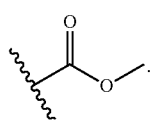 [SMILES: *C(=O)OC]

3. The method of claim 1, wherein $R_1$ is —CN.

4. The method of claim 1, wherein the source of cyanide is NaCN.

5. The method of claim 1, wherein the source of cyanide is KCN.

6. The method of claim 1 further comprising purifying the product of the step of reacting by recrystallization.

7. The method of claim 1 further comprising purifying the product of the step of reacting by column chromatography.

8. The method of claim 1 further comprising purifying the product of the step of reacting by distillation.

* * * * *